(12) United States Patent
Chen et al.

(10) Patent No.: US 11,137,463 B2
(45) Date of Patent: Oct. 5, 2021

(54) SYSTEM AND METHOD FOR CONTINUOUS WAVE CONSTANT AMPLITUDE ON-RESONANCE AND OFF-RESONANCE SPIN-LOCK FOR MAGNETIC RESONANCE IMAGING

(71) Applicant: The Chinese University of Hong Kong, Hong Kong SAR (CN)

(72) Inventors: Weitian Chen, Hong Kong SAR (CN); Baiyan Jiang, Jakarta (ID)

(73) Assignee: The Chinese University of Hong Kong, Hong Kong (CN)

( * ) Notice: Subject to any disclaimer, the term of this patent is extended or adjusted under 35 U.S.C. 154(b) by 1104 days.

(21) Appl. No.: 15/663,254

(22) Filed: Jul. 28, 2017

(65) Prior Publication Data
US 2018/0031661 A1 Feb. 1, 2018

Related U.S. Application Data

(60) Provisional application No. 62/369,627, filed on Aug. 1, 2016.

(51) Int. Cl.
*A61B 5/05* (2021.01)
*G01R 33/56* (2006.01)
(Continued)

(52) U.S. Cl.
CPC .......... *G01R 33/5602* (2013.01); *A61B 5/055* (2013.01); *G01R 33/446* (2013.01);
(Continued)

(58) Field of Classification Search
None
See application file for complete search history.

(56) References Cited

U.S. PATENT DOCUMENTS

2010/0237866 A1* 9/2010 Liimatainen .......... G01R 33/50
324/309

OTHER PUBLICATIONS

Chen et al., "Quantitative $T_{1\rho}$ Imaging Using Phase Cycling for $B_0$ and $B_1$ Field Inhomogeneity Compensation," Magnetic Resonance Imaging 29 (2011) 608-619.
(Continued)

*Primary Examiner* — Joel F Brutus
(74) *Attorney, Agent, or Firm* — Kilpatrick Townsend & Stockton

(57) ABSTRACT

MRI techniques provide robust imaging in the presence of inhomogeneity in the B1 (RF) and/or B0 magnetic fields. The techniques include using a magnetization prep sequence that includes an adiabatic half passage (AHP) followed by a spin-lock pulse, followed by a reverse AHP, after which a data acquisition sequence can be applied. The AHP and reverse AHP can have amplitude and frequency modulated to sweep through a region of frequency space. The RF amplitude of the AHP and reverse AHP can be designed to be equal to the spin-lock amplitude. Quantification of a magnetization relaxation parameter (e.g., T1rho) can use a modified relaxation model that accounts for relaxation effects during the reverse AHP. A dual-acquisition technique in which the reverse AHP of the second magnetization prep sequence has opposite frequency modulation to the reverse AHP of the first magnetization prep sequence can also be used.

37 Claims, 29 Drawing Sheets
(21 of 29 Drawing Sheet(s) Filed in Color)

(51) Int. Cl.
*G01R 33/565* (2006.01)
*A61B 5/055* (2006.01)
*G01R 33/44* (2006.01)
*G01R 33/50* (2006.01)
*A61B 5/00* (2006.01)

(52) U.S. Cl.
CPC .......... *G01R 33/50* (2013.01); *G01R 33/565* (2013.01); *G01R 33/5659* (2013.01); *G01R 33/56563* (2013.01); *A61B 5/4244* (2013.01)

(56) References Cited

OTHER PUBLICATIONS

Chen et al., "Breath-hold Black Blood Quantitative t1rho Imaging of Liver Using Single Shot Fast Spin Echo Acquisition,"Quant Imaging Med Surg 2016; 6(2):168-177.

Larson et al., "Using Aqdiabatic Inversion Pulses for Long-$T_2$ Supression in Ultrashort Echo Time (UTE) Imaging," Magnetic Resonance in medicine 58:952-961 (2007).

Norris et al., "An Analysis of the Effects of Short $T_2$ Values on the Hyperbolic-Secant Pulse," Journal of Magnetic Resonance 92. 94-101 (1991).

Silver et al., "Highly Selective $\pi/2$ and $\pi$ Pulse Generation," Journal of Magnetic Resonance 59, 347-351 (1984).

Trott et al., "$R_{1\rho}$ Relaxation Outside of the Fast-Exchange Limit," Communications, Journal of Magnetic Resonance 154, 157-160 (2002).

Witschey II, et al., "Artifacts in T1p-weighted Imaging: Compensation for $B_1$ and $B_0$ Field Imperfections," Journal of Magnetic Resonance, 186, (2007) 75-85.

Zaiss, et al., "Exchange-Dependent Relaxation in the Rotating Frame for Slow and Intermediate Exchange—Modeling Off-Resonant Spin-Lock and Chemical Exchange Saturation Transfer," NMR in Biomedicine, 2013; 26: 507-518.

\* cited by examiner

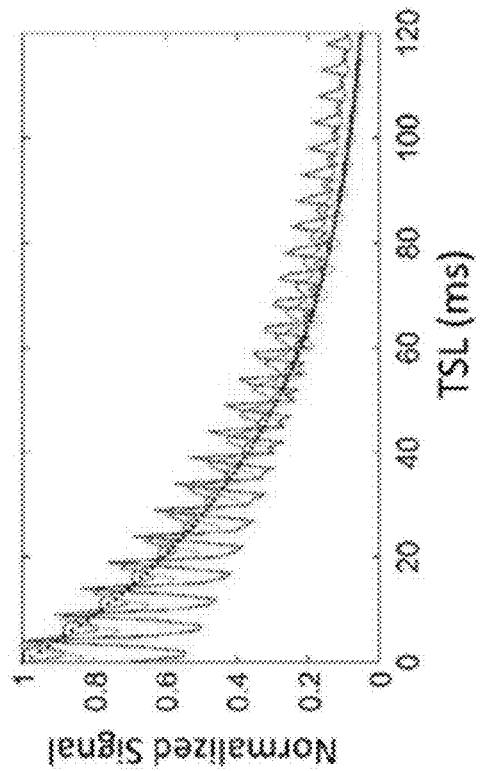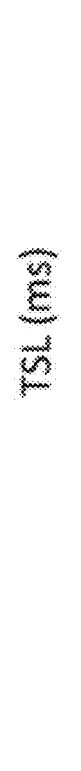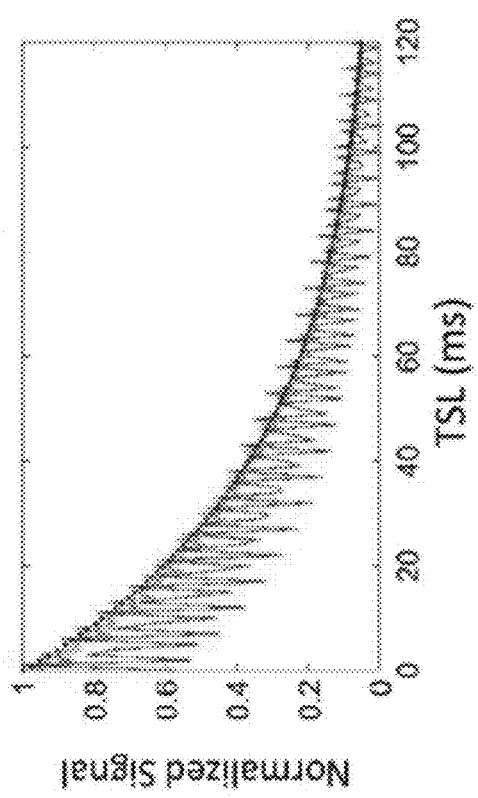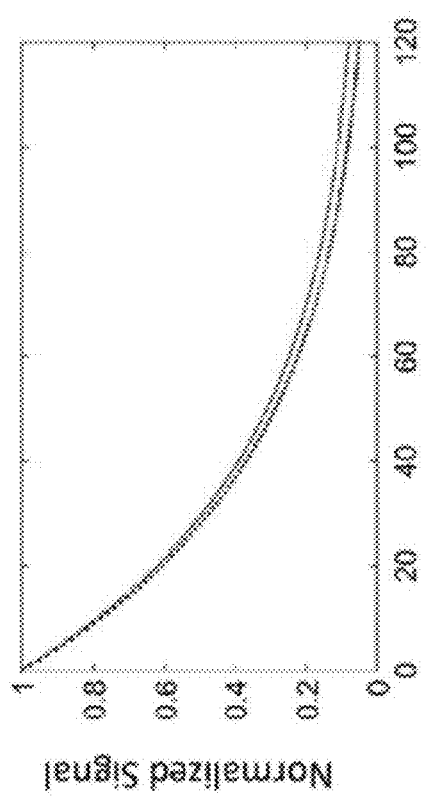
FIG. 10A (prior art)
FIG. 10B (prior art)
FIG. 10C
FIG. 10D

SYSTEM AND METHOD FOR CONTINUOUS WAVE CONSTANT AMPLITUDE ON-RESONANCE AND OFF-RESONANCE SPIN-LOCK FOR MAGNETIC RESONANCE IMAGING

CROSS-REFERENCE TO RELATED APPLICATION

This application claims the benefit of U.S. Provisional Application No. 62/369,627, filed Aug. 1, 2016, the disclosure of which is incorporated by reference herein in its entirety.

BACKGROUND

This disclosure relates generally to magnetic resonance imaging (MRI) techniques, and in particular to techniques for continuous wave constant amplitude on-resonance and off-resonance spin lock that are robust in the presence of system imperfections such as spatial inhomogeneity in the B1 radio-frequency (RF) and B0 fields. Such techniques can be used, for example, in T1rho imaging and quantification as well as other imaging biomarkers.

Magnetic resonance imaging (MRI) is a noninvasive diagnostic technique that can allow assessments of the composition and state of various tissues. In an MRI procedure, a patient is placed in a strong longitudinal magnetic field (B0) that aligns nuclear spins of atoms in the patient's body, producing a net magnetization vector. RF pulses with magnetic field components (B1) transverse to the longitudinal field and frequencies tuned to the Larmor frequency of an isotope of interest (often $^1$H) are applied. These pulses can flip spins into a higher energy state, resulting in a transverse component to the magnetization vector. As these spins return to the ground state, responsive RF pulses from the patient's body can be detected. Based on the response to pulses, characteristics of the magnetization can be measured. Commonly used measurements include the spin-lattice relaxation time (T1), measurement of which is typically based on recovery of the longitudinal component of the magnetization vector, and the spin-spin relaxation time (T2), measurement of which is typically based on decay of the transverse component of the magnetization vector. Since different anatomical structures have different material compositions, quantification of T1 and/or T2 can provide information about the material composition of a structure being imaged, and particular pulse sequences can be optimized to quantify T1 or T2. MRI has been used to achieve high-resolution images of a variety of anatomical structures, including organs and other tissues.

A quantifiable spin-relaxation parameter that is the subject of recent interest is the spin-lattice relaxation time in the rotating frame (T1rho, or T1ρ. For T1rho measurement, an RF pulse, referred to as a spin-lock pulse, is applied to lock the magnetization around an effective magnetic field. The parameter T1rho characterizes the decay (or relaxation) rate of spins during the spin-lock process. In clinical use, T2 and T1rho may provide complementary diagnostic information.

One challenge for T1rho imaging and other spin-lock based imaging methods is that spatial inhomogeneity in the B1 RF and/or B0 fields may cause failure of spin-lock in certain regions, resulting in image artifacts, such as banding effects. This can reduce the diagnostic utility of the images.

SUMMARY

Certain embodiments of the present invention relate to techniques for robust imaging in the presence of system imperfections such as inhomogeneity in the B1 (RF) and/or B0 magnetic fields. In some embodiments, the technique includes using a "magnetization prep" sequence that includes an adiabatic half passage (AHP) followed by a spin-lock pulse, followed by a reverse AHP, after which a data acquisition sequence can be applied. The adiabatic half-passage can be a pulse sequence with amplitude and frequency modulated to sweep through a region of frequency space. The modulation can be based on hyperbolic secant or other functions, and the RF amplitude of the AHP and reverse AHP can be designed to be equal to the spin-lock amplitude. Magnetization prep sequences as described herein can be used to effectively align the magnetization with the spin-lock field for both on-resonance and off-resonance spin-lock frequencies. Such magnetization prep sequences can be used in connection with T1 rho-weighted imaging as well as other MRI processes that rely on spin-lock.

In some embodiments, a relaxation effect due to the reverse AHP may result in non-negligible error when using a mono-exponential relaxation model to determine T1rho from sets of image data. This error can be reduced or eliminated by modifying the relaxation model to include an additional constant term that takes into account the relaxation effect.

In some embodiments, magnetization oscillation due to violation of the adiabatic condition may result in non-negligible error in determination of T1rho (or other spin-lock based imaging biomarkers) from sets of image data. This error can be reduced by using a dual-acquisition approach for on-resonance spin-lock. A first acquisition can use a first T1rho prep sequence that includes an AHP prior to the spin-lock pulse and a reverse AHP following the spin-lock pulse. The second acquisition can use the same AHP and spin-lock sequence followed by an "inverted" (or "opposite") version of the reverse AHP in which a frequency ramp-up is used instead of ramp-down (or vice versa). Complex image data acquired from the two acquisitions can be subtracted to provide a T1rho-weighted image, and sets of such images can be analyzed using a mono-exponential relaxation model or modified relaxation model with an additional constant term to determine T1rho.

The following detailed description, together with the accompanying drawings, provides a further understanding of the nature and advantages of the claimed invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 10A-10D show examples of simulation results, showing the normalized magnetization signal as a function of time of spin lock (TSL) for various techniques including PCCSL (FIG. 10A), Witschey's method (FIG. 10B); a single-acquisition approach according to an embodiment of the present invention (FIG. 10C); and dual-acquisition approach according to an embodiment of the present invention (FIG. 10D).

DETAILED DESCRIPTION

Figure 1:
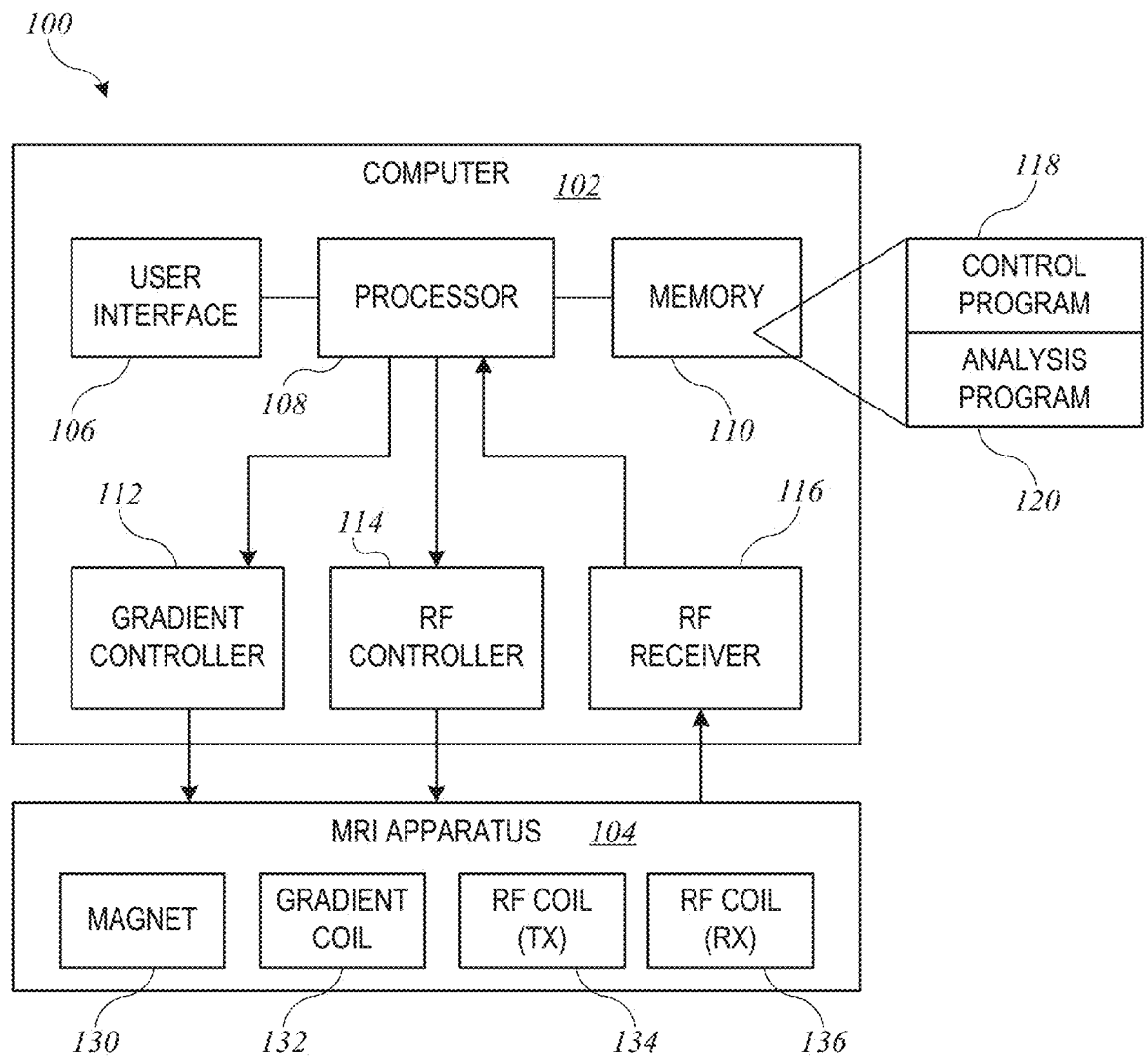
FIG. 1 shows an MRI system that can be used in connection with practicing some embodiments of the present invention.

FIG. 1 shows an MRI system that can be used in connection with practicing some embodiments of the present invention. MRI system 100 includes a computer 102 communicably coupled to an MRI apparatus 104.

Computer 102 can be of generally conventional design and can include a user interface 106, a processor 108, a memory 110, a gradient controller 112, an RF controller 114, and an RF receiver 116. User interface 106 can include components that allow a user (e.g., an operator of MM system 100) to input instructions or data and to view information. For example, user interface 106 can include a keyboard, mouse, joystick, display screen, touch-sensitive display screen, and so on. Processor 108 can include a general purpose programmable processor (or any other processor or set of processors) capable of executing program code instructions to perform various operations. Memory 110 can include a combination of volatile and nonvolatile storage elements (e.g., DRAM, SRAM, flash memory, magnetic disk, optical disk, etc.). Portions of memory 110 can store program code to be executed by processor 108. Examples of the program code can include a control program 118, which can coordinate operations of MRI apparatus 104 as described below in order to acquire data, and an analysis program 120, which can perform analysis algorithms on data acquired from MRI apparatus 104. Gradient controller 112, RF controller 114, and RF receiver 116 can incorporate standard communication interfaces and protocols to communicate with components of MRI apparatus 104 as described below.

MM apparatus 104 can be of generally conventional design and can incorporate a magnet 130, a gradient coil 132, and RF coils 134, 136. Magnet 130 can be a magnet capable of generating a large constant magnetic field B0 (e.g., 1.5 T, 3.0 T, or the like) in a longitudinal direction, in a region where a patient (or other subject to be imaged) can be placed. Gradient coil 132 can be capable of generating gradients in the constant magnetic field B0; operation of gradient coil 132 can be controlled by computer 102 via gradient controller 112. RF coils 134, 136 can include a transmitter (TX) coil 134 and a receiver (RX) coil 136. In some embodiments, a single coil can serve as both transmitter and receiver. In some embodiments, RF transmitter coil 134 can be placed around the portion of the subject's body that is to be imaged while RF receiver coil 136 is placed elsewhere within MRI apparatus 104. The preferred placement of RF coils 134, 136 may depend on the specific portion of the body that is to be imaged; those skilled in the art with access to the present disclosure will be able to make appropriate selections.

In operation, computer 100 can drive gradient coil 132 using gradient controller 112 to shape the magnetic field around the region being imaged. Computer 100 can drive RF transmitter coil 134 using RF controller 114 to generate RF pulses at a resonant frequency for an isotope of interest, driving nuclear spins into an excited state. RF receiver coil 136 can detect RF waves generated by the spins relaxing from the excited state when RF pulses are not being generated. RF receiver 116 can include amplifiers, digital-to-analog converters, and other circuitry to generate digital data from the RF waves detected by RF receiver coil 136. RF receiver 116 can provide this data to processor 108 for analysis.

MM system 100 is illustrative, and many variations and modifications are possible. Those skilled in the art will be familiar with a variety of MRI apparatus and control systems and with basic principles of MRI data acquisition, including the use of gradient fields and RF pulses, as well as techniques for detecting signals responsive to RF pulses and processing those signals to generate images.

In some embodiments, MRI system 100 or other MRI apparatus can be used to generate pulse sequences suitable for T1rho imaging of a subject, such as a specific organ or tissue within a patient. Examples of pulse sequences and imaging operations are described below.

Typical MRI imaging processes include a "preparation" phase and an "acquisition" phase. During the preparation phase, various pulse sequences can be generated in RF transmitter coil 136 to create a desired state of the magnetization vectors of nuclei of interest. For instance, a "reset" sequence may be used to reset net magnetization such that net magnetization becomes zero. Other types of preparation can include pulse sequences designed to suppress signals from specific types of tissue not of interest (e.g., blood, fat). For imaging techniques based on spin-lock, such as T1rho imaging, the preparation phase can include a magnetization prep sequence, which locks the magnetization around an effective magnetic field. In the case of T1rho, the effective magnetic field has a transverse component. Thereafter, acquisition can be performed using various sequences such as fast spin echo sequences or other sequences as desired.

In embodiments described herein, a magnetization prep sequence for T1rho imaging (referred to as a "T1rho prep sequence") includes a spin-lock RF pulse of constant amplitude and frequency. During spin lock, spins follow a constant T1rho decay. By collecting T1rho-weighted images with different time of spin-lock (TSL), the T1rho value can be measured by fitting the collected images to a monoexponential relaxation model. While examples herein focus on T1rho imaging, it is to be understood that similar techniques can be used for other imaging technologies based on spin-lock.

In certain embodiments of the present invention, the magnetization prep sequence also incorporates adiabatic pulses that can reduce the effects of system imperfections, including B1 RF and B0 field inhomogeneity. For instance, an adiabatic half passage (AHP) can be performed before the spin-lock RF pulse, and a reverse AHP can be performed after the spin-lock RF pulse. The adiabatic pulses can simultaneously compensate for B1 and B0 field inhomogeneity, provided that the RF amplitude of the AHP (and reverse AHP) is equal to the spin-lock amplitude. In some embodiments, the RF amplitude of the AHP (and reverse AHP) is considered equal to the spin-lock amplitude if the following condition is satisfied exactly or approximately:

$$\omega_1^{max} = \omega_{sl}, \quad (1)$$

where $\omega_1(t) = \gamma B_1(t)$ is the amplitude of field B1 in radians/second, $\gamma$ is the gyromagnetic ratio for the nuclear species of interest, $\omega_1^{max}$ is the maximum B1 amplitude of the AHP and reverse AHP in radians/second, and $\omega_{sl}$ is the expected constant spin-lock frequency in radians per second. When the condition of Eq. (1) holds, at the end of the AHP, the magnetization at location r is oriented at an angle ($\theta$) from the longitudinal direction given by:

$$\theta(r) = \tan^{-1} \frac{\tilde{\omega}_{sl}(r)}{\Delta\omega_0(r)}, \quad (2)$$

where $\Delta\omega_0(r)$ is the spatial distribution of B0 field inhomogeneity and $\tilde{\omega}_{sl}(r)$ is the spatial distribution of the actual spin-lock frequency, which is the expected spin-lock frequency $\omega_{sl}$ as influenced by B1 inhomogeneity. The amplitude of the spin-lock RF pulse and the B0 field do not vary during the time of spin-lock, and as a result, the magnetization at each location r is locked at the corresponding orientation angle $\theta(r)$. After the spin-lock pulse, the reverse AHP, which can have symmetric amplitude and frequency modulation to the AHP, returns magnetization to the longitudinal direction. Consequently, even in the presence of B0 and B1 field inhomogeneity, the magnetization prep sequence can result in images without banding artifacts.

Eq. (2) assumes that the constant amplitude spin-lock RF pulse is applied at the on-resonance frequency of water (or more generally another on-resonance frequency of interest). In some embodiments, a constant amplitude spin-lock RF pulse may be applied at an off-resonance frequency. Where the spin-lock RF pulse is applied at off-resonance frequency that differs from resonance by $\Delta\omega_c$, under the condition of Eq. (1), the spins will be locked at an angle given by:

$$\theta(r) = \tan^{-1}\left(\frac{\tilde{\omega}_{sl}(r)}{\Delta\omega_c + \Delta\omega_0(r)}\right). \quad (3)$$

Based on the analysis above, it can be demonstrated that, when an AHP and reverse AHP are used, the spins at each location will be locked at $\theta(r)$, resulting in no signal oscillation and no banding artifacts even in the presence of spatial inhomogeneity in B1 and B0 fields.

Figure 2A:
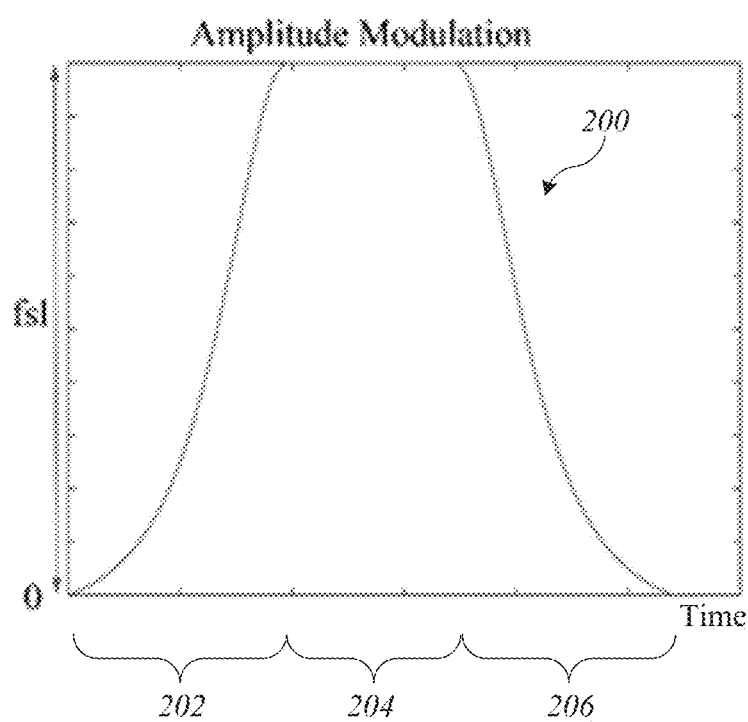
FIGS. 2A-2C show schematic diagrams of characteristics of RF pulse clusters that can be used in a T1rho prep sequence according to an embodiment of the present invention.
Figure 2B:
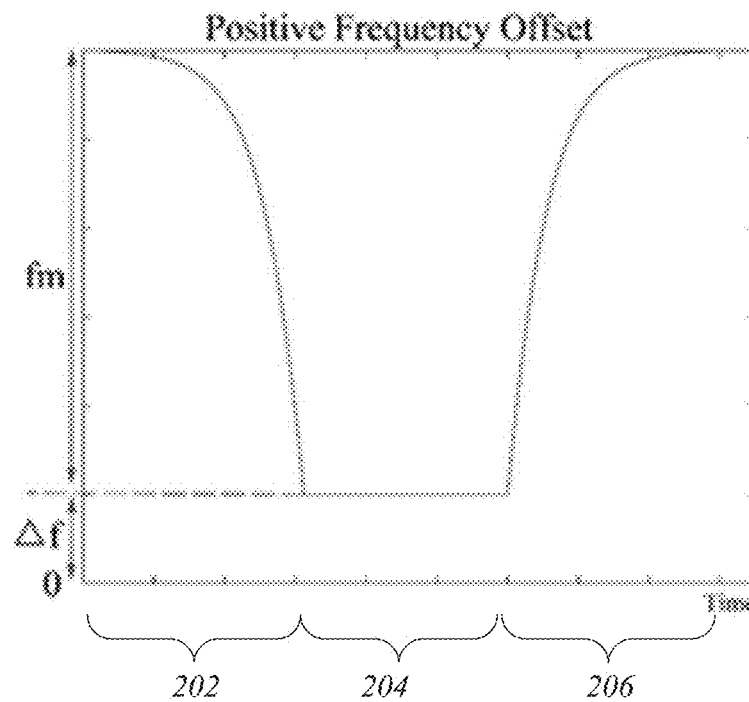
Figure 2C:
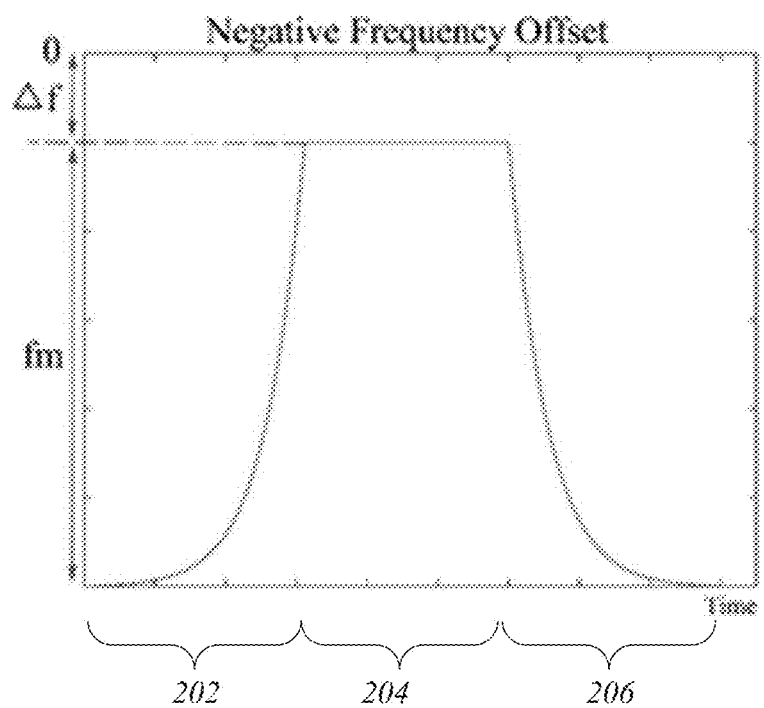

FIGS. 2A-2C show schematic diagrams of characteristics of RF pulse clusters that can be used in a magnetization prep sequence according to an embodiment of the present invention. FIG. 2A shows an amplitude modulation waveform 200; FIG. 2B shows a frequency modulation waveform 210 with a positive frequency offset ($\Delta f$) from resonance and maximum frequency amplitude fm; and FIG. 2C shows a frequency modulation waveform 220 with a negative frequency offset from resonance and maximum frequency amplitude fm. (For on-resonance spin-lock, frequency offset $\Delta f$ goes to zero.) It is to be understood that amplitude modulation waveform 200 can be used with either frequency modulation waveform 210 or frequency modulation waveform 220. Waveforms 200, 210, 220 each include an AHP (segment 202), a spin-lock pulse of duration TSL (segment 204), and a reverse AHP (segment 206). AHP segment 202 can be an HS1 or "stretched" HSn pulse based on a hyperbolic secant function, e.g., as described in Silver et al., "Highly selective $\pi/2$ and $\pi$ pulse generation," *J. Magn. Reson.* 59:347-531 (1984). For an HS1 pulse, the amplitude modulation (AM) and frequency modulation (FM) for AHP segment 202 can be expressed as:

$$\omega_1(t) = \omega_1^{max} \text{sech}\left(\beta\left(\frac{t}{T_p} - 1\right)\right) \text{ and} \quad (4)$$

$$\Delta\omega(t) = \omega_{RF}(t) - \omega_0 = 2\pi A_0 \tanh\left(\beta\left(\frac{t}{T_p} - 1\right)\right), \quad (5)$$

where $A_0$ is the amplitude of the frequency sweep in Hertz, $\omega_0$ is the Larmor frequency, $\beta$ is a dimensionless coefficient; $T_p$ is the pulse duration of the AHP; and time t is in the range $[0, T_p]$. Amplitude and frequency modulations for reverse AHP segment 206 can be obtained by time-reversing the modulations for AHP segment 202.

In some embodiments, e.g., with relatively low spin-lock frequency, it may be difficult to use the HS1 pulse to satisfy the condition specified by Eq. (1) and maintain the adiabatic condition. Accordingly, "stretched" HSn pulses can be used. The amplitude modulation (AM) and frequency modulation (FM) for AHP segment 202 using HSn pulses can be expressed as:

$$\omega_1(t) = \omega_1^{max} \mathrm{sech}\left(\beta\left(\frac{t}{T_p} - 1\right)^n\right) \text{ and} \quad (6)$$

$$\Delta\omega(t) = \omega_{RF}(t) - \omega_0 = 2\pi A_0 \int_0^t \left[\tanh\left(\beta\left(\frac{u}{T_p} - 1\right)^n\right)\right]^2 du. \quad (7)$$

As before, amplitude and frequency modulations for reverse AHP segment 206 can be obtained by time-reversing the modulations for AHP segment 202.

Figure 3A:
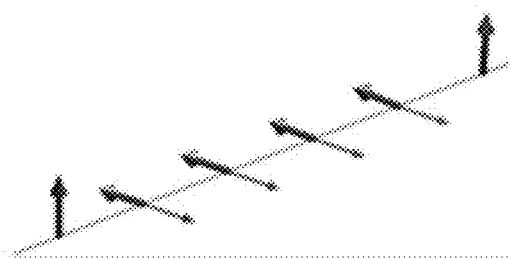
FIGS. 3A-3E show simulated magnetization evolution during spin-lock for conventional spin-lock methods using a very short hard RF pulse (FIGS. 3B, 3C, 3E) and for a method using AHP and reverse AHP according to an embodiment of the present invention (FIGS. 3A, 3D).
Figure 3B:
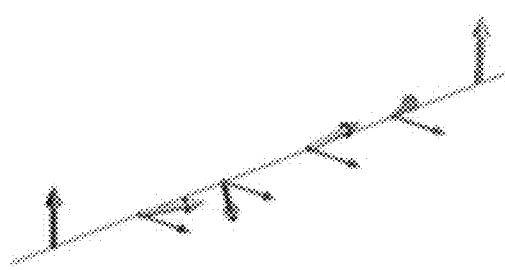
Figure 3C:
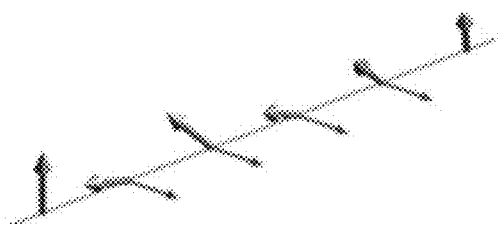
Figure 3D:
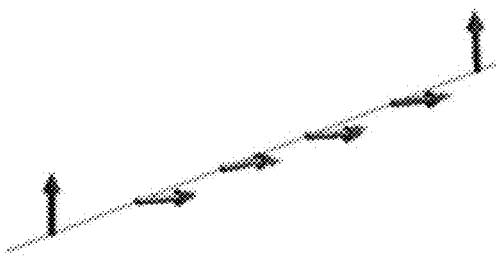
Figure 3E:
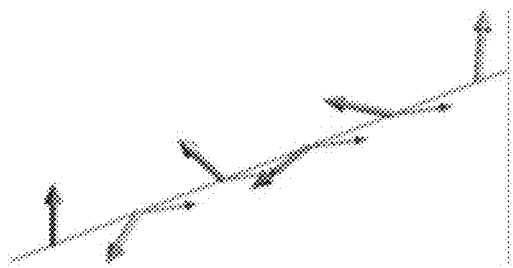

RF clusters of the kind shown in FIGS. 2A-2C can be used to effectively align the magnetization with the spin-lock field, for both on-resonance and off-resonance spin-lock frequencies. By way of illustration, FIGS. 3A-3E show simulated magnetization evolution during spin-lock for conventional methods (using a very short hard RF pulse) and for a method using AHP and reverse AHP according to an embodiment of the present invention. FIGS. 3A-3C correspond to an spin-lock at offset from resonance of −100 Hz, with a B1 RF field that is 90% of the expected value and B0 field inhomogeneity of −200 Hz. FIG. 3A shows the evolution of the magnetization spin (blue arrows) and the effective spin-lock field (purple arrows) for a method using AHP and reverse AHP as described herein. FIGS. 3B and 3C show the evolution of the magnetization spin (green arrows) and the effective spin-lock field (purple arrows) for a conventional approach under the same conditions as FIG. 3A. Two cases are shown because, at negative frequency offset, the conventional approach can result in magnetization flipping either by a large flip angle so that the effective spin-lock field is parallel to the magnetization (shown in FIG. 3B) or by a small flip angle so that the effective spin-lock field is antiparallel to the magnetization (shown in FIG. 3C). FIGS. 3D and 3E correspond to spin-lock at an offset from resonance of +100 Hz, with a B1 RF field that is 90% of the expected value and B0 field inhomogeneity of −200 Hz. FIG. 3D shows the evolution of the magnetization spin (blue arrows) and the effective spin-lock field (purple arrows) for a method using AHP and reverse AHP as described herein. FIG. 3E shows the evolution of the magnetization spin (green arrows) and the effective spin-lock field (purple arrows) for a conventional approach under the same conditions as FIG. 3D. As can be seen, the conventional approach (FIGS. 3B, 3C, 3E) results in magnetization deviating from the effective spin-lock field, while the approach described herein (FIGS. 3A, 3D) results in magnetization being effectively aligned with the effective spin-lock field at both positive and negative frequency offset.

Figure 4:
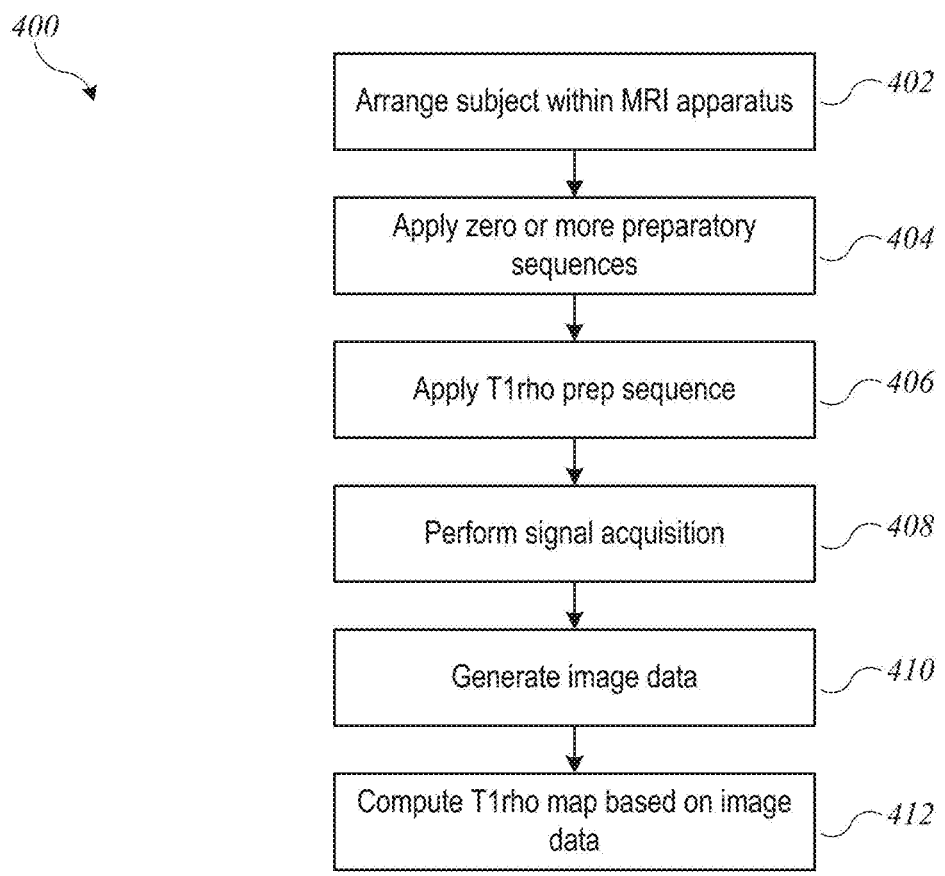
FIG. 4 shows a flow diagram of a process 400 for T1rho imaging according to an embodiment of the present invention.

Magnetization prep sequences that include an AHP and a reverse AHP can be used in MRI processes. FIG. 4 shows a flow diagram of a single-acquisition process 400 for T1rho imaging according to an embodiment of the present invention. (T1rho is used as an example, but process 400 can be applied in other imaging techniques.) Process 400 can be performed using an MRI apparatus such as MRI apparatus 100 of FIG. 1. At block 402, a subject (e.g., a patient whose tissue is to be imaged) is arranged within an MRI apparatus. This can include having the patient assume a supine or other desired position and aligning the patient within the MRI apparatus. In some embodiments, this may also include positioning of RF and/or gradient coils; the particular positioning will depend on what is being imaged.

At block 404, various preparatory pulse sequences can be applied. Examples include magnetization reset sequences, suppression sequences to reduce the effect of selected tissue types (e.g., blood, fat, etc.), and the like. Such sequences can be conventional and are optional; a detailed description is omitted as not being critical to understanding the claimed invention.

At block 406, a T1rho prep sequence can be applied. The T1rho prep sequence can include an AHP, a spin-lock pulse with duration TSL, and a reverse AHP. For example, the T1rho prep sequence can have amplitude and frequency modulation characteristics as described above with reference to FIGS. 2A and 2B, or with reference to FIGS. 2A and 2C. Other modulation profiles can be substituted, provided that Eq. (1) and the adiabatic condition are satisfied.

At block 408, signal acquisition can be performed. Signal acquisition can include generating RF pulses to stimulate a signal from the subject and operating an RF receiver coil to detect the signal. Various acquisition sequences can be performed, including single-shot or multi-shot fast spin echo (FSE) sequences; other acquisition sequences and techniques suitable for quantifying T1rho can also be used. During the signal acquisition, a data set can be collected.

At block 410, image data can be generated based on the data set collected during the signal acquisition. Conventional techniques for generating the image data can be applied; examples include Fourier transform of acquired k-space data. At block 412, based on the image data, a T1rho map indicating T1rho values for various points in the image can be computed. In some embodiments, multiple T1 rho-weighted images can be generated by repeating portions of process 400 using different TSL values, and T1rho values can be determined by fitting the image data to a relaxation (or decay) model. In some embodiments, a mono-exponential relaxation model may be used for T1rho quantification. However, as described below, a mono-exponential relaxation model may be inaccurate due to relaxation effects during the reverse AHP. Accordingly, some embodiments of the present invention may incorporate a modified relaxation model that reduces such inaccuracy; examples are described below.

Figure 5A:
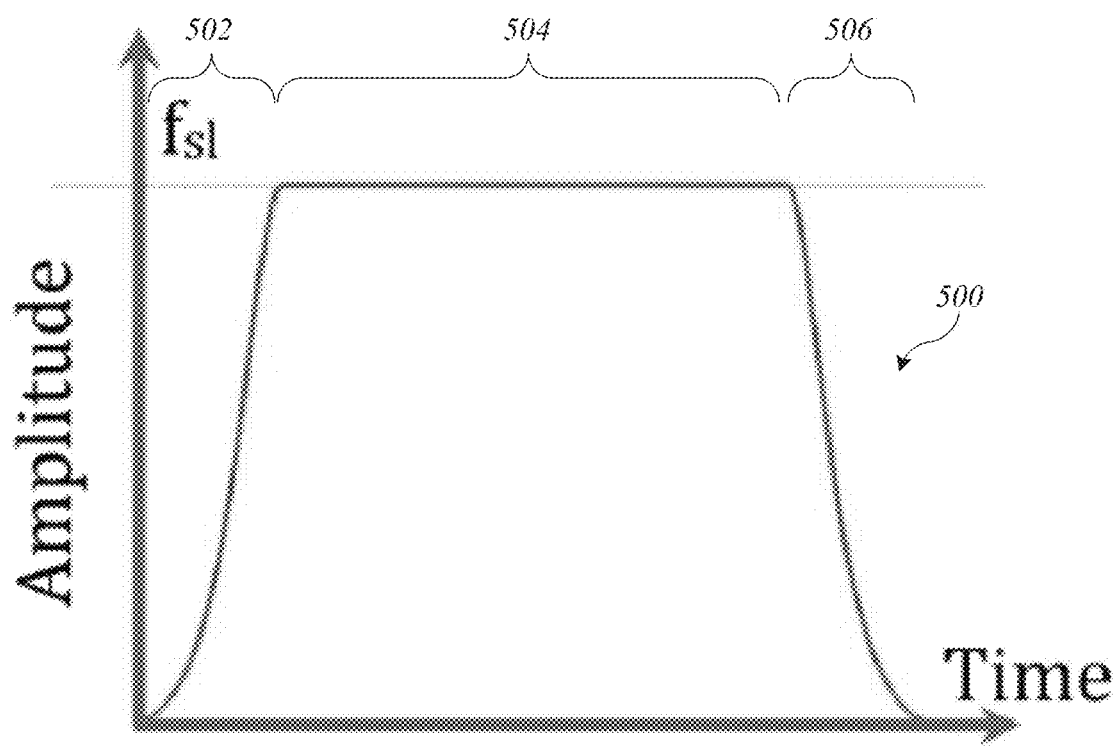
FIGS. 5A-5C show schematic diagrams of characteristics of RF pulse clusters that can be used in T1rho prep sequences according to an embodiment of the present invention that uses two acquisitions.
Figure 5B:
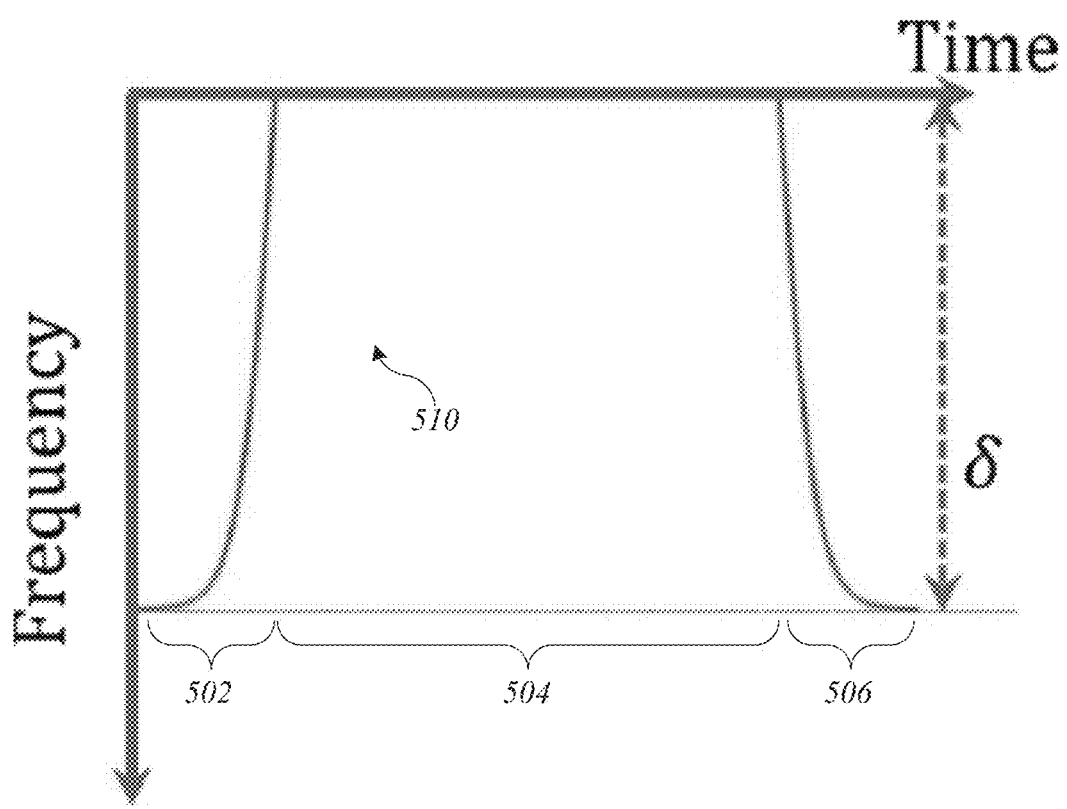
Figure 5C:
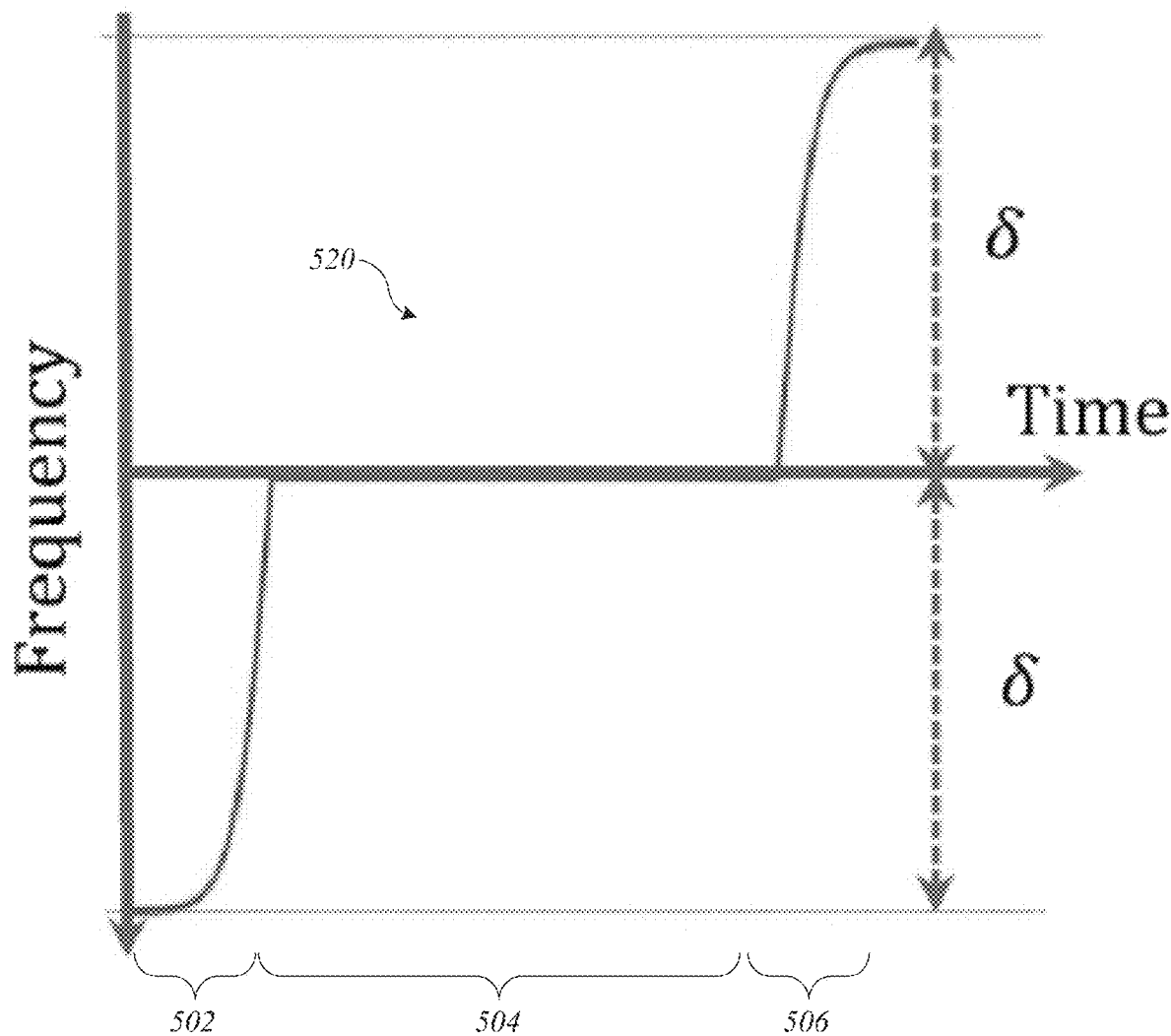

Process 400 is an example of a "single-acquisition" approach that can be used for T1rho quantification for either on-resonance or off-resonance spin-lock according to an embodiment of the present invention. A related approach uses two signal acquisitions with on-resonance spin-lock. Each signal acquisition is preceded by a T1rho prep sequence. The first T1rho prep sequence can be as described above (for the on-resonance case, where $\Delta f=0$). The second T1rho prep sequence can be identical to the first, except that the frequency modulation of the reverse AHP segment is opposite to that of the first reverse AHP segment. FIGS. 5A-5C show schematic diagrams of characteristics of RF pulse clusters that can be used in T1rho prep sequences according to an embodiment of the present invention that uses two acquisitions. FIG. 5A shows an amplitude modulation waveform 500 that can be used for both T1rho prep sequences. FIG. 5B shows a frequency modulation waveform 510 that can be used for a first T1rho prep sequence, and FIG. 5C shows a frequency modulation waveform 520 that can be used for a second T1rho prep sequence. The AHP (segment 502) and spin-lock pulse (segment 504) of waveforms 500 and 510 can be identical to corresponding segments 202, 204 of frequency modulation waveforms 200 and 210 of FIGS. 2A and 2B (for the on-resonance case). As shown in FIG. 5C, reverse AHP (segment 606) of frequency modulation waveform 520 can be opposite to reverse AHP segment 506 of frequency modulation waveform 510. Each T1rho prep sequence can be followed by a signal acquisition. Complex image data obtained during the signal acquisitions can be subtracted from each other, reducing the error in measured T1rho.

Figure 6:
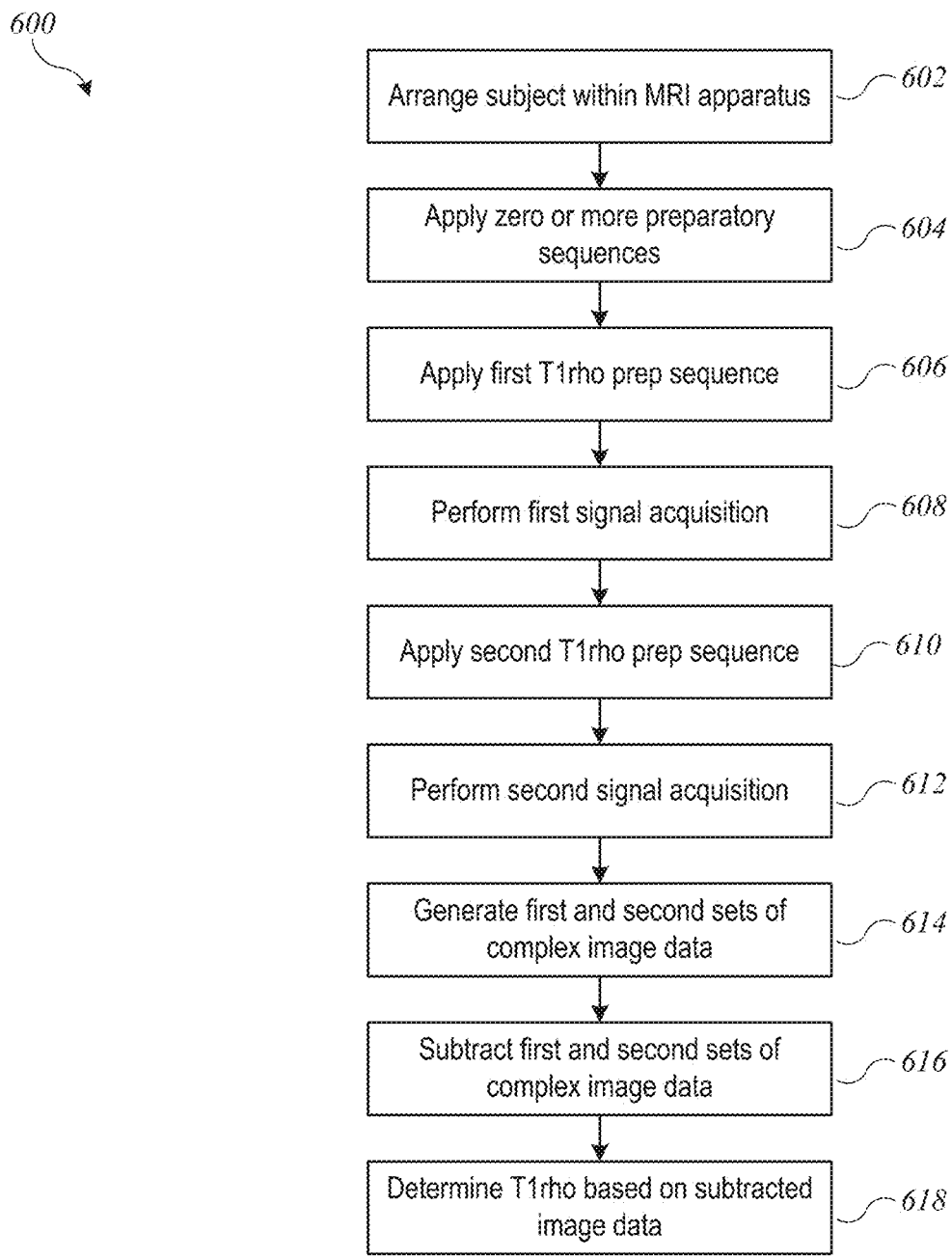
FIG. 6 shows a flow diagram of a dual-acquisition process for T1rho imaging according to an embodiment of the present invention.

FIG. 6 shows a flow diagram of a dual-acquisition process 600 for T1rho imaging according to an embodiment of the present invention. Process 600 can be performed using an MRI apparatus such as MRI apparatus 100 of FIG. 1. At block 602, a subject (e.g., a patient whose tissue is to be imaged) is arranged within an MRI apparatus. This can include having the patient assume a supine or other desired position and aligning the patient within the MRI apparatus. In some embodiments, this may also include positioning of RF and/or gradient coils; the particular positioning will depend on what is being imaged.

At block 604, various preparatory sequences can be applied. Examples include magnetization reset sequences, suppression sequences to reduce the effect of selected tissue types (e.g., blood, fat, etc.), and the like. Such sequences can be conventional and are optional; a detailed description is omitted as not being critical to understanding the claimed invention.

At block 606, a first T1rho prep sequence can be applied. The first T1rho prep sequence can include an AHP, a spin-lock pulse with duration TSL, and a reverse AHP. For example, the first T1rho prep sequence can have amplitude and frequency modulation characteristics as described above with reference to FIGS. 5A and 5B. Other modulation profiles can be substituted, provided that Eq. (1) and the adiabatic condition are satisfied.

At block 608, a first signal acquisition can be performed, similarly to block 308 of FIG. 3.

At block 610, a second T1rho prep sequence can be applied. The second T1rho prep sequence can include an AHP, a spin-lock segment with duration TSL, and a reverse AHP. The AHP and spin-lock pulse of the second T1rho prep sequence can be identical to corresponding segments of the first T1rho prep sequence. The reverse AHP can have frequency modulation opposite to the reverse AHP of the first T1rho prep sequence (block 606). For example, if the first T1rho prep sequence uses the amplitude and frequency modulation characteristics described above with reference to FIGS. 5A and 5B, then the second T1rho prep sequence can use the amplitude and frequency modulation characteristics described above with reference to FIGS. 5A and 5C. (The order in which different T1rho prep sequences are applied is not critical.) As at block 606, other modulation profiles can be substituted, provided that Eq. (1) and the adiabatic condition are satisfied.

At block 612, a second signal acquisition can be performed. The acquisition sequence(s) are preferably the same as those used at block 608.

At block 614, first and second sets of complex image data can be generated based on the first and second signal acquisitions, respectively. Conventional techniques for generating the image data can be applied separately to each of the first and second signal acquisitions; examples include Fourier transform of acquired k-space data. At block 616, a subtraction operation can be performed to subtract the first set of complex image data from the second set of complex image data (or vice versa). Based on the subtracted image data, a T1rho map indicating T1rho values for various points in the image can be determined. In some embodiments, multiple T1 rho-weighted images can be generated by repeating portions of process 600 using different TSL values; T1rho can be determined by fitting the image data to a relaxation model.

The AHP and reverse AHP may satisfy the adiabatic condition, which states that:

$$K = \frac{\sqrt{|\omega_1(t)|^2 + |\Delta\omega(t)|^2}}{\frac{d}{dt}\left(\tan^{-1}\frac{\omega_1(t)}{\Delta\omega(t)}\right)} \gg 1. \tag{8}$$

Figure 7:
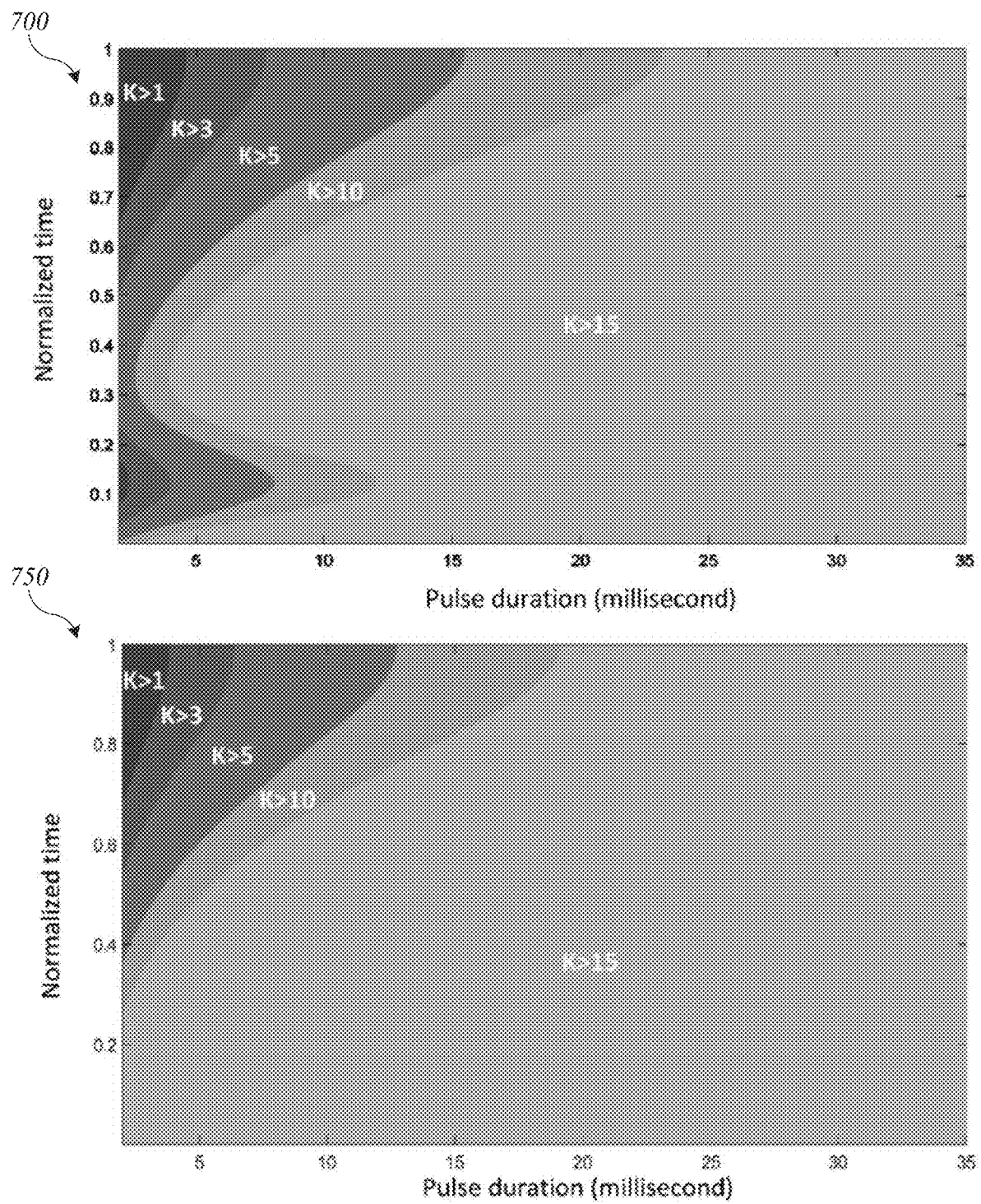
FIG. 7 shows two plots of pulse duration $T_p$ (in milliseconds) vs. a normalized time ($t/T_p$) and indicates the value of a parameter K, for two different HSn pulses.

This condition results in a prolonged pulse duration $T_p$ at a reduced maximum B1 amplitude $\omega_1^{max}$. FIG. 7 shows two plots of pulse duration $T_p$ (in milliseconds) vs. a normalized time ($t/T_p$) and indicates the value of K computed according to Eq. (8), for two different HSn pulses. Plot 700 is computed using HS8 AHP at a spin-lock frequency ($2\pi\omega_{sl}$) of 250 Hz. Plot 750 is computed using HS1 AHP at a spin-lock frequency of 500 Hz. As shown, at lower spin-lock frequency, a longer $T_p$ is required to satisfy the adiabatic condition.

In part because of the pulse duration $T_p$, the monoexponential relaxation model conventionally used in T1rho quantification may not be entirely accurate. Conventionally, T1rho relaxation can be described using a two-pool model based on the Bloch-McConnell equations (an example is described in O. Trott et al., "R1rho Relaxation Outside of the Fast-Exchange Limit," *J. Magn. Reson.* 14:157-160 (2002)). From this model, the general solution of magnetization at the end of spin-lock can be expressed as:

$$M(t) = \sum_{n=1}^{6} e^{\lambda_n t} l_n + S \tag{9}$$

where $\lambda_n$ is the nth eigenvalue of the matrix from the Bloch-McConnell equations, $l_n$ is a term proportional to the corresponding eigenvectors, and S is a constant term representing the stationary solution. In many cases, the spin relaxation is dominated by a single exponential damping, and Eq. (9) can be simplified to:

$$M(t) = e^{\lambda \cdot t} l + S \tag{10}$$

By substituting boundary conditions, Eq. (10) can be written as:

$$M(tsl) = (M_{ini} - M_{ss})e^{-R_1\rho tsl} + M_{ss} \tag{11}$$

where $M_{ini}$ is the magnetization at the beginning of spin-lock, $R_{1\rho}$ is ($1/T_{1\rho}$), tsl is the time of spin-lock, and $M_{ss}$ is the stationary solution. The stationary solution $M_{ss}$ can be expressed (see Zaiss et al., "Exchange-Dependent Relaxation in the Rotating Frame for Slow and Intermediate Exchange—Modeling Off-Resonant Spin-Lock and Chemical Exchange Saturation Transfer," NMR in Biomedicine 26.5:507-518 (2012)) as:

$$M_{ss} = -\frac{p_z R_{1a} \cos\theta}{R_{1\rho}} \quad (12)$$

where $\theta$ is determined by Eq. (2) or (3), $p_z=1$ for spin-lock experiments, and $R_{1a}$ is $R_1$ ($=1/T1$) of pool A. For on-resonance imaging, $\theta$ is 90 degrees, the stationary solution is essentially zero, and Eq. (11) can be simplified to a mono-exponential relaxation model:

$$M(tsl) = Ae^{-R_{1\rho}tsl} \quad (13)$$

which is commonly used for T1rho quantification.

Eq. (13) is a reasonable approximation for conventional methods of achieving spin-lock, where a very short hard RF pulse is used to tip magnetization into a longitudinal direction. The relaxation effect during this short pulse is negligible, and the mono-exponential decay model of Eq. (13) can be used for T1rho quantification. However, for adiabatic pulse sequences (e.g., as shown in FIGS. 2A-2C or FIGS. 5A-5C), due to the relatively long duration of reverse AHP segment 210, the relaxation effect during reverse AHP segment 210 can cause the final magnetization to deviate from the relaxation model of Eq. (13). Further, since the stationary solution is neglected in Eq. (13), there will also be some degree of error introduced when performing T1rho quantification at off-resonance spin-lock.

To reduce this error, in some embodiments of the present invention, the influence on the magnetization due to relaxation during the reverse AHP, for both on-resonance and off-resonance spin-lock, can be characterized approximately by:

$$M_e(tsl) = Ae^{-R_{1\rho}tsl} + B \quad (14)$$

where $M_e(tsl)$ is the longitudinal magnetization at the end of the reverse AHP, and A and B are terms independent of tsl. The term B is different from the stationary solution $M_{ss}$ in Eq. (11) and is nonzero on resonance; it is also different from terms introduced in some analyses for noise characterization.

It can be shown that, for on-resonance spin-lock, the B term is due to the relaxation effect during the reverse AHP and that, for off-resonance spin-lock, the B term is due to a combinatorial effect of the relaxation effect during the reverse AHP and the stationary solution $M_{ss}$ at off-resonance spin-lock. The relaxation during the AHP does not affect the relaxation model if the AHP ensures that the magnetization is tipped into the direction of the spin-lock field under the adiabatic condition.

The adiabatic pulse response in the presence of relaxation can be effectively predicted by full equation Bloch simulation based on the hard-pulse approximation. (See, e.g., Norris et al., "An analysis of the effects of short T2 values on the hyperbolic-secant pulse," *J. Magn. Reson.* 92:94-101 (1991); Larson et al., "Using adiabatic inversion pulses for long-T2 suppression in ultrashort echo time (UTE) imaging," *Magn. Reson. Med.* 58(5): 952-961 (2007).) By solving the Bloch equation using the following general solution, it is possible to express the effect of the reverse AHP on its input signal as:

$$M(t) = \begin{pmatrix} e^{-t/T2} & 0 & 0 \\ 0 & e^{-t/T2} & 0 \\ 0 & 0 & e^{-t/T1} \end{pmatrix} R_{z'}(\omega_0 t) M_i + \begin{pmatrix} 0 \\ 0 \\ R \end{pmatrix} \quad (15)$$

where $R_{z'}(\omega_0 t)$ is the rotation matrix for adiabatic pulses, $R = M_0(1-e^{-t/T1})$, and $M_i$ is the initial magnetization for the ith interval. Since the adiabatic pulses have a continuous waveform, Eq. (15) can be solved by a hard pulse approximation. For the first interval, the initial magnetization $M_1$ is the magnetization after the spin-lock process, which is in the form of Eq. (14). For the general case, the initial magnetization is:

$$M_1 = \begin{pmatrix} \left(a_1 e^{-R_{1\rho}tsl} + b_1\right)\sin\theta \\ 0 \\ \left(a_2 e^{-R_{1\rho}tsl} + b_2\right)\cos\theta \end{pmatrix} \quad (16)$$

where $\theta$ is determined by Eq. (2) or (3).

It can be shown that the magnetization after the first interval is:

$$M_2 = \begin{pmatrix} e^{-t/T2}\left[(A_4 a_1 + A_2 a_2)e^{-R_{1\rho}tsl} + A_1 b_1 + A_2 b_2\right] \\ e^{-t/T2}\left[(-A_4 a_1 + A_3 a_2)e^{-R_{1\rho}tsl} - A_4 b_1 + A_3 b_2\right] \\ -e^{-t/T1}\left[(A_6 a_1 + A_5 a_2)e^{-R_{1\rho}tsl} + A_6 b_1 + A_5 b_2\right] - R \end{pmatrix} \quad (17)$$

where:
$A_1 = \sin\theta\,(\cos\alpha\,\cos^2\xi + \sin^2\xi)$,
$A_2 = \cos\xi\,\sin\alpha\,\cos\theta$,
$A_3 = \cos\alpha\,\cos\theta$,
$A_4 = \cos\xi\,\sin\alpha\,\sin\theta$,
$A_5 = \sin\xi\,\sin\alpha\,\cos\theta$, and
$A_6 = \cos\xi\,\sin\xi\,\sin\theta\,(\cos\alpha - 1)$, where $\alpha$ is the precession angle and $\xi$ is the angle between the magnetization and the z-axis. It can be seen from Eq. (17) that $M_2$ has the same form as Eq. (14). Accordingly, Eq. (17) can be rewritten as:

$$M_2 = \begin{pmatrix} c_1 e^{-R_{1\rho}tsl} + d_1 \\ c_2 e^{-R_{1\rho}tsl} + d_2 \\ c_3 e^{-R_{1\rho}tsl} + d_3 \end{pmatrix} \quad (18)$$

It can also be shown that the magnetization after the second interval is:

$$M_3 = \quad (19)$$
$$\begin{pmatrix} e^{-t/T2}\left[(B_1 c_1 + B_2 c_2 - B_3 c_3)e^{-R_{1\rho}tsl} + B_1 d_1 + B_2 d_2 - B_3 d_3\right] \\ e^{-t/T2}\left[(-B_5 c_1 + B_4 c_2 + B_6 c_3)e^{-R_{1\rho}tsl} - B_5 d_1 + B_4 d_2 - B_6 d_3\right] \\ -e^{-t/T1}\left[(B_9 c_1 + B_7 c_2 - B_8 c_3)e^{-R_{1\rho}tsl} + B_9 d_1 + B_7 d_2 - B_8 d_3\right] - R \end{pmatrix}$$

where
$B_1 = \cos\alpha\,\cos^2\xi + \sin^2\xi$,
$B_2 = B_5 = \cos\xi\,\sin\alpha$,
$B_3 = B_9 = \cos\xi\,\sin\xi(\cos\alpha - 1)$,
$B_4 = \cos\alpha$,
$B_6 = B_7 = \sin\alpha\,\sin\xi$, and
$B_8 = \cos\alpha\,\sin^2\xi + \cos^2\xi$.

Therefore, for any input in the form of Eq. (14), the magnetization after the reverse AHP will take the same form.

Examples: Simulation Studies

To illustrate the benefits of the techniques described herein, simulation studies were conducted using the full equation Bloch simulation. The signal was simulated as a function of TSL under varying conditions of B0 and B1 field inhomogeneity. One simulation was conducted for T1=900 ms, T2=35 ms, T1rho=40 ms, T2rho=70 ms, and spin-lock frequency of 500 Hz. The AHP and reverse AHP each had duration of 25 ms, with $A_0$=500 Hz and $\beta$=4.

Figure 8A:
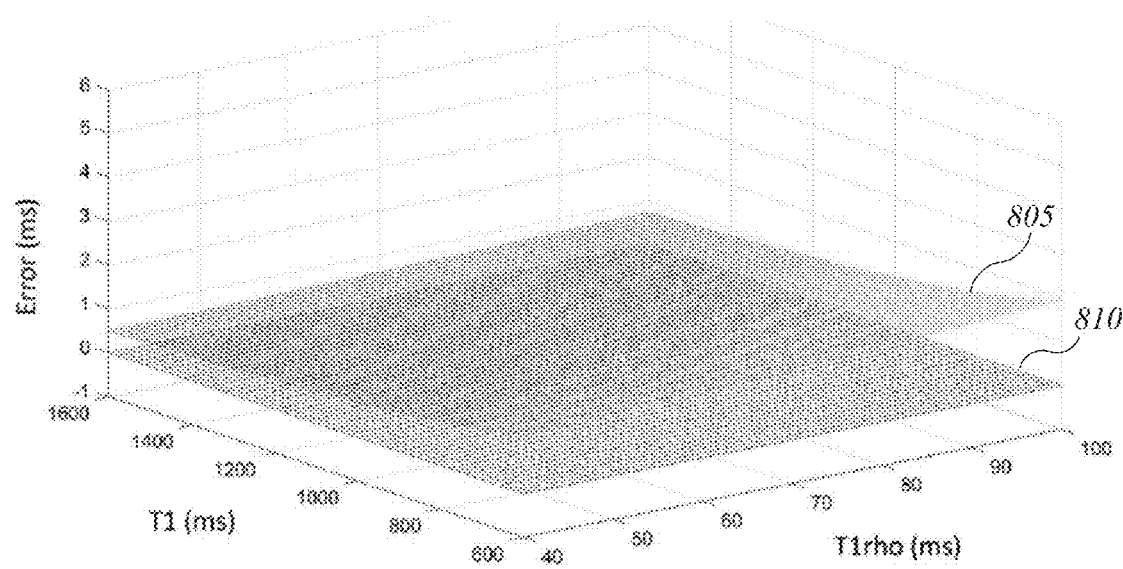
FIGS. 8A and 8B show three-dimensional sheet plots of error in measured T1rho (vertical axis) as a function of actual T1rho and T1, based on Bloch simulation for various embodiments of the present invention.
Figure 8B:
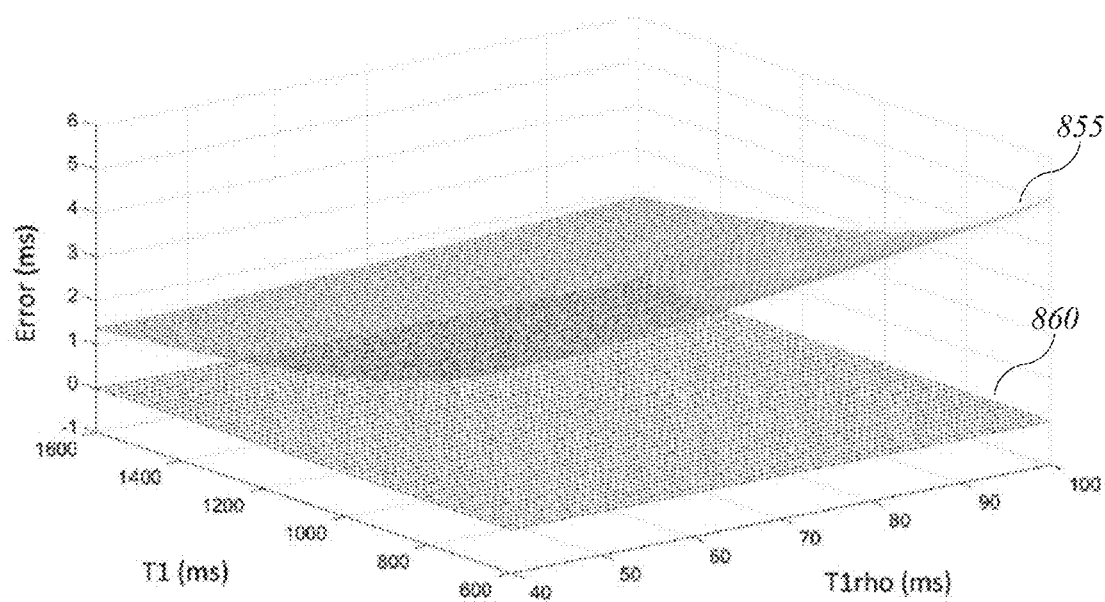

One simulation study demonstrated an effect of the dual-acquisition approach. FIGS. 8A and 8B show three-dimensional sheet plots of the error in measured T1rho (vertical axis) as a function of actual T1rho and T1, based on Bloch simulation for various embodiments of the present invention using on-resonance spin-lock. Initial magnetization, prior to the reverse AHP, is generated using Eq. (13). Magnetization after the reverse AHP is calculated based on full Bloch equation simulation. In this study, a conventional mono-exponential relaxation model (Eq. (13)) was used to estimate T1rho for data sets simulated using both single-acquisition and dual-acquisition approaches. In FIG. 8A, sheet plots 805 (for a single-acquisition approach) and 810 (for a dual-acquisition approach) were computed for a reverse AHP with duration $T_p$=10 ms. In FIG. 8B, sheet plots 855 (for a single-acquisition approach) and 860 (for a dual-acquisition approach) were computed for a reverse AHP with duration $T_p$=25 ms. For the single-acquisition approach, the measured T1rho deviates from the actual value, and the deviation becomes more pronounced with longer pulse duration (sheet plot 805 compared to sheet plot 855) and for shorter T1 values. The dual-acquisition approach (sheet plots 810 and 860) shows reduced error in measured T1rho relative to the single-acquisition approach.

Figure 9A:
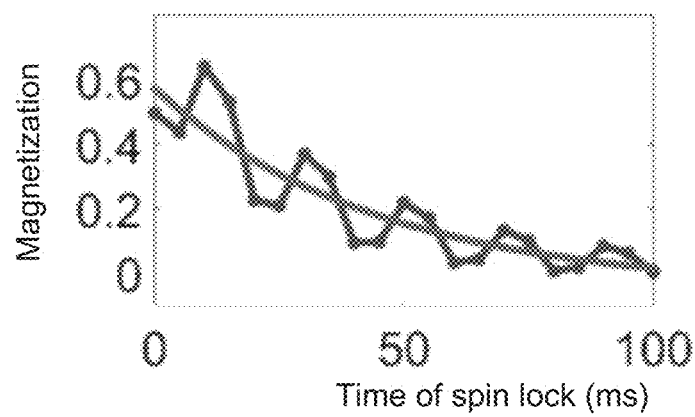
FIGS. 9A-9D show magnetization as a function of time of spin-lock for single-acquisition and dual-acquisition approaches according to various embodiment of the present invention.
Figure 9B:
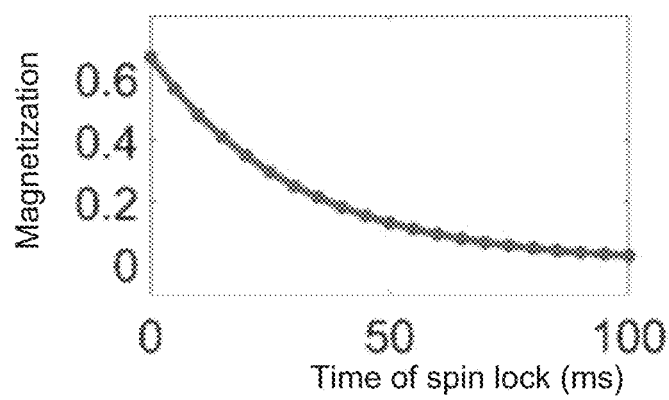
Figure 9C:
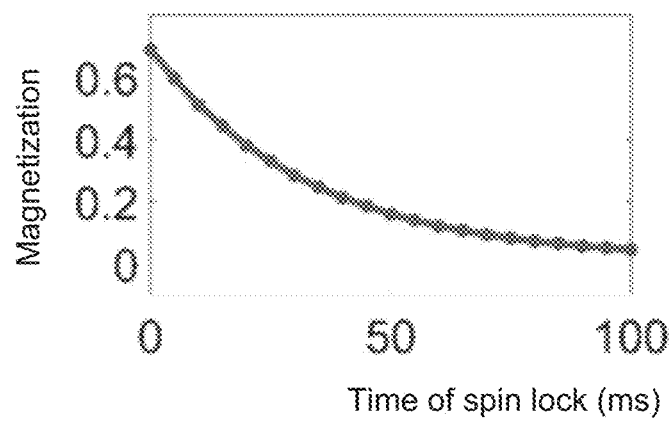
Figure 9D:
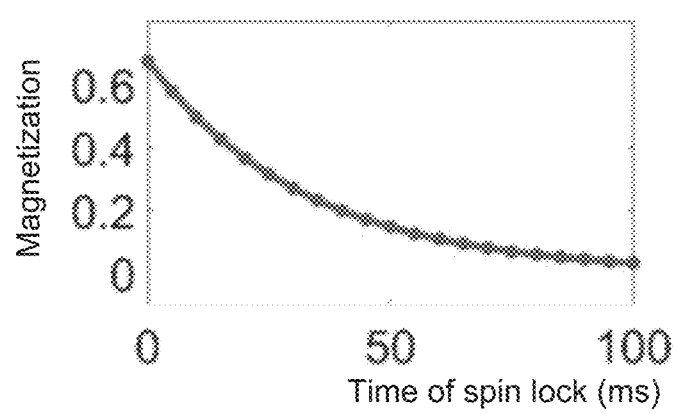
Figure 11A:
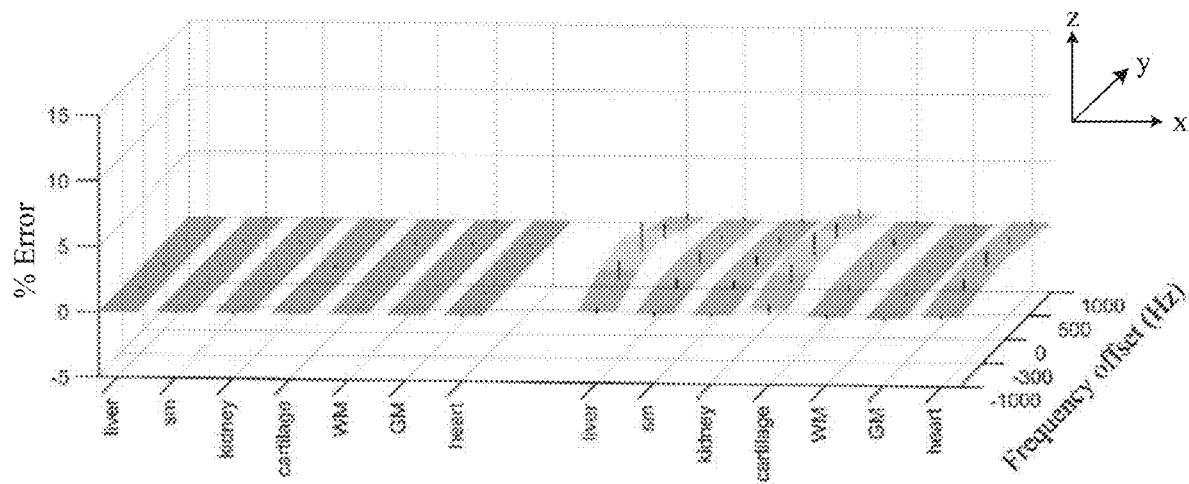
FIGS. 11A-11F are 3-D sheet graphs summarize the resulting errors for various tissue types under different conditions of the pulse sequence, including for pulse sequences according to various embodiments of the present invention.
Figure 11B:
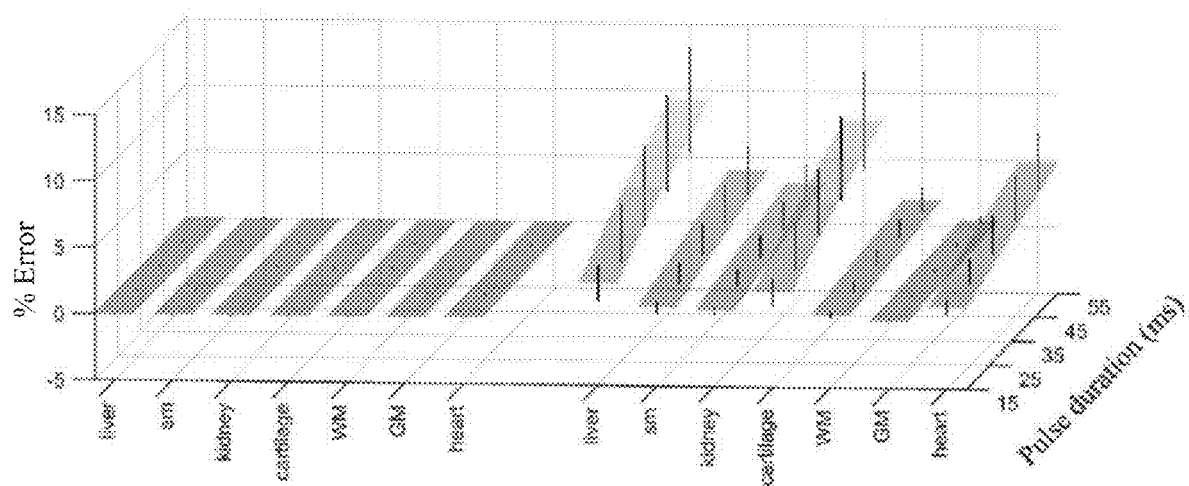
Figure 11C:
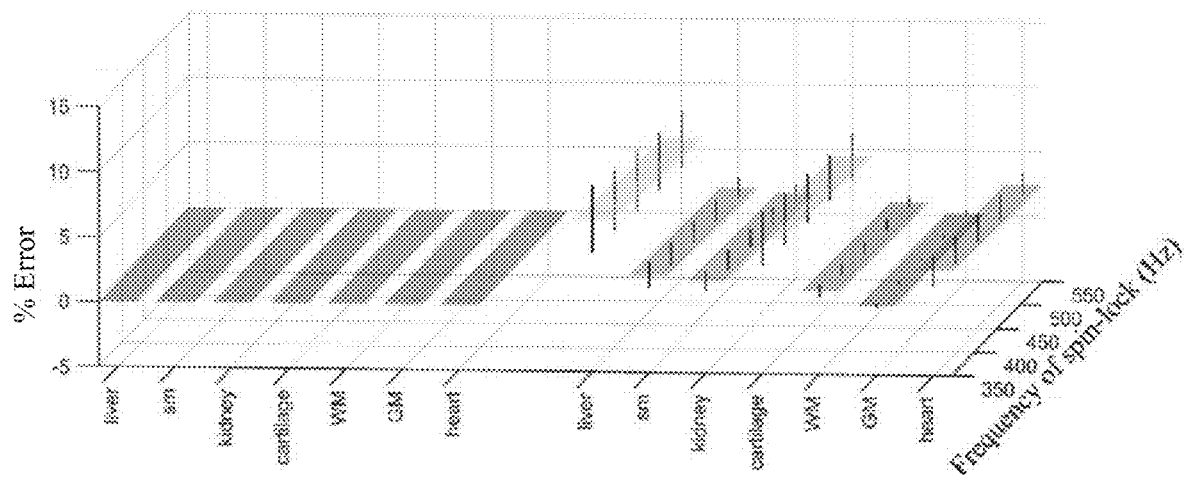
Figure 11D:
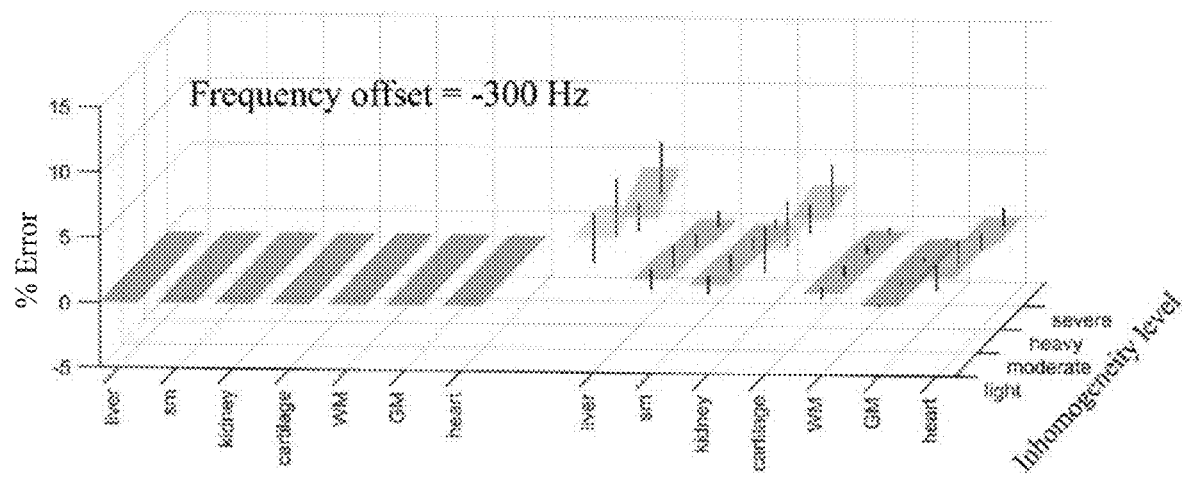
Figure 11E:
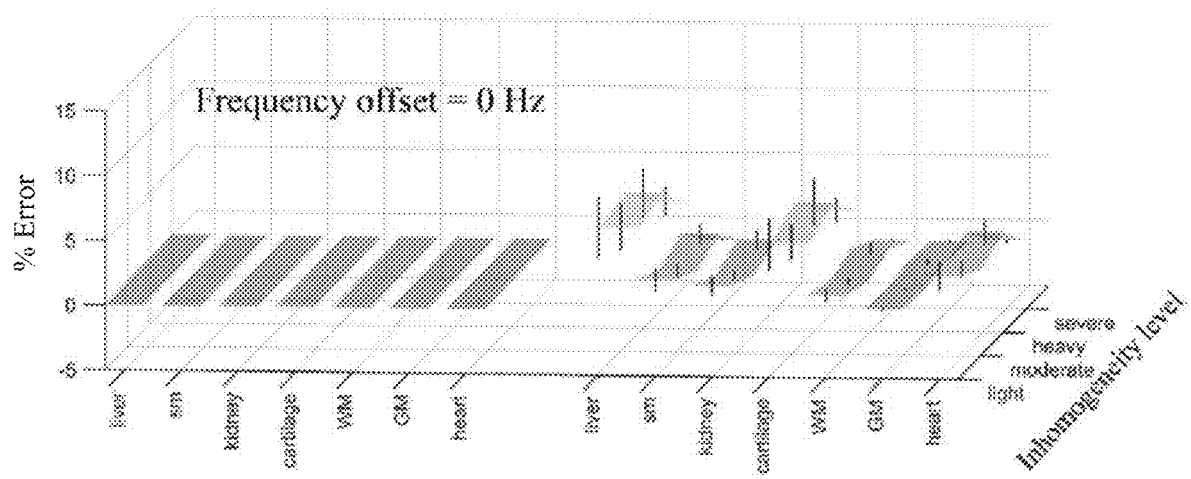
Figure 11F:
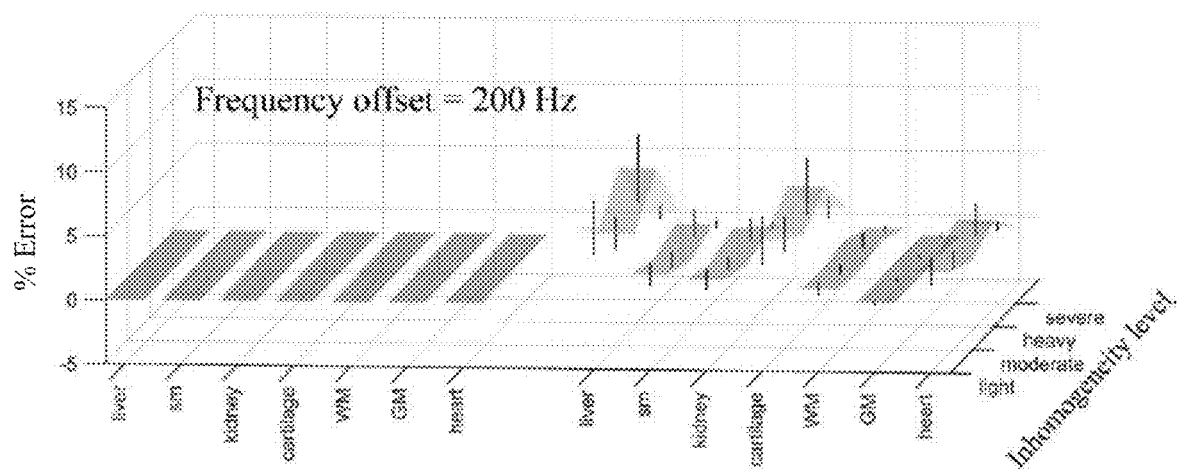

When the adiabatic condition is violated, the magnetization may not align with the effective spin-lock field, and magnetization may start oscillating. The dual-acquisition approach may mitigate signal oscillation during spin-lock in cases where the adiabatic condition is violated. This has been explored in a simulation study in which simulated data under different conditions were fit using the modified relaxation model of Eq. (14). This simulation used a two-pool Bloch-McConnell equation with the following parameters: average T1/T2 1500/35 ms; population of pool A (water) 0.99; population of pool B (metabolite) 0.01; chemical shift of pool B 200 Hz. FIGS. 9A-9D show magnetization as a function of time of spin-lock for single-acquisition and dual-acquisition approaches according to various embodiment of the present invention. In each case, the red curve shows the fitting results, and the blue curve shows the simulated data with blue dots representing actual simulated data points. FIG. 9A shows results for a single-acquisition approach with AHP and reverse AHP of duration $T_p$=10 ms, spin-lock frequency 250 Hz. FIG. 9B shows results for a dual-acquisition approach with AHP and reverse AHP of duration $T_p$=10 ms, spin-lock frequency 250 Hz. FIG. 9C shows results for a single-acquisition approach with AHP and reverse AHP of duration $T_p$=25 ms, spin-lock frequency 500 Hz. FIG. 9D shows results for a single-acquisition approach with AHP and reverse AHP of duration $T_p$=25 ms, spin-lock frequency 500 Hz. The single-acquisition approach follows the relaxation model in FIG. 9C, but in FIG. 9A, oscillations in the magnetization can be seen due to violation of the adiabatic condition. The dual-acquisition approach mitigates these oscillations, as can be seen in FIG. 9B.

Simulation results produced using techniques described herein were also compared to two published approaches for T1rho imaging that also attempt to provide compensation for inhomogeneity in fields B1 and B0. The first conventional approach, referred to herein as "Witschey's method," combines a rotary echo approach with a 180-degree refocusing pulse (as described in Witschey et al., "Artifacts in T1ρ weighted imaging: Compensation for B1 and B0 field imperfections," *J. Magn. Reson.* 186:75-85 (2007)). The second conventional approach, referred to herein as "PCCSL," uses phase cycling and a composite RF pulse approach (as described in Chen et al., "Quantitative T1rho imaging using phase cycling for B0 and B1 field inhomogeneity," *Magn. Reson. Imaging* 29:608-619 (2011)). FIGS. 10A-10D show examples of simulation results, showing the normalized magnetization signal as a function of time of spin lock (TSL) for various techniques. FIG. 10A shows results for PCCSL; FIG. 10B shows results for Witschey's method; FIG. 10C shows results for a single-acquisition approach according to an embodiment of the present invention using the mono-exponential relaxation model of Eq. (13); and FIG. 10D shows results for a dual-acquisition approach according to an embodiment of the present invention also using the mono-exponential relaxation model of Eq. (13). In each case, the true T1rho exponential decay is shown as a black dotted line. Simulations were run under four different inhomogeneity scenarios: (1) off-resonance frequency of 100 Hz, actual B1 field 80% of expected B1 field (blue solid line); (2) off-resonance frequency of −100 Hz, actual B1 field 80% of expected B1 field (red solid line); (3) off-resonance frequency of 200 Hz, actual B1 field 70% of expected B1 field (yellow solid line); and (4) off-resonance frequency of −200 Hz, actual B1 field 70% of expected B1 field (magenta solid line). As can be seen, the conventional techniques (FIGS. 10A and 10B) result in signal oscillations when the actual conditions deviate significantly from ideal, and the oscillations may depend on the polarity (positive or negative) of the off-resonance frequency. In contrast, the results in FIGS. 10C and 10D, obtained based on the single-acquisition and dual-acquisition techniques described herein, do not result in signal oscillation. It is to be understood that these simulation results and all other results shown herein are intended to illustrate advantages that may be obtained using certain embodiments of the present invention and are not intended to be limiting.

To further compare the conventional and modified relaxation models, another simulation study was performed using simulations of seven types of human tissue: liver (T1=812 ms, T2=42 ms); skeletal muscle (sm) (T1=1412 ms, T2=50 ms); kidney (T1=1194 ms, T2=56 ms); cartilage (T1=1156 ms, T2=43 ms); white matter (wm) (T1=1084 ms, T2=69 ms); gray matter (gm) (T1=1820 ms, T2=99 ms); and heart (T1=1471 ms, T2=47 ms). Simulations were performed to generate data using maximum TSL of 200 ms at various resonance frequency offsets for spin-lock (−1000 Hz, −300 Hz, 0 Hz, 500 Hz, 1000 Hz), various durations of AHP and reverse AHP (15 ms, 25 ms, 35 ms, 45 ms, 55 ms), and various frequencies of spin-lock (350 Hz, 400 Hz, 450 Hz, 500 Hz, 550 Hz). Various cases of system imperfections (light to severe field inhomogeneity) were also simulated at on-resonance frequency and offsets of −100 Hz and +200 Hz. For each scenario, the simulated data were fitted to the relaxation model of Eq. (14) using various TSL lengths (65 ms, 75 ms, 80 ms) and various numbers of TSLs ranging from 4 to 50. The same data were also fitted to the conventional relaxation model of Eq. (13). The error at each TSL is calculated as:

$$\text{error} = \left| \frac{y(TSL) - \widehat{y(TSL)}}{y(TSL)} \right| \quad (20)$$

where y(TSL) is the estimated data resulting from the fit and $\widehat{y(TSL)}$ is the simulated or input data. The maximum error provides a metric to assess the performance of the relaxation models.

FIGS. 11A-11F are 3-D sheet graphs summarize the resulting errors for various tissue types under different conditions of the pulse sequence. In each figure, error is shown on the z axis. Different tissue types are identified on the x axis; the left group of seven sheets show the results for each tissue type fitted to the modified relaxation model of Eq. (14), and the right group of seven sheets show the results for each tissue type fitted to the mono-exponential relaxation model of Eq. (13). The sheets are color-coded based on error value, with purple representing error closest to zero and yellow representing maximum observed error. In each figure, the y axis corresponds to a different variable condition of the simulation: in FIG. 11A, frequency offset from resonance is varied; in FIG. 11B, pulse duration; in FIG. 11C, frequency of spin-lock; in FIG. 11D, field inhomogeneity levels at frequency offset from resonance of −300 Hz; in FIG. 11E, field inhomogeneity levels at frequency offset of 0 Hz (on-resonance); and in FIG. 11F, field inhomogeneity levels at frequency offset of +200 Hz. As can be seen from FIGS. 11A-11F, fitting to the modified relaxation model of Eq. (14) yields low error under all conditions, while the error in fitting to the mono-exponential relaxation model of Eq. (13) exhibits significant dependence on the conditions of data acquisition. It should be noted that the fitting to Eq. (13) does not account for the non-zero stationary solution at off-resonance spin-lock, and in FIGS. 11A and 11D-11F, the errors are due to a combination of the stationary solution and relaxation effects for off-resonance spin-lock.

Another simulation study used a 3-pool Bloch-McConnell equation with magnetization transfer for pulse sequences including AHP and reverse AHP according to an embodiment of the present invention. The 3-pool model included chemical exchange and magnetization transfer effects during the entire magnetization evolution. Tissue parameters included: T1=812 ms; T2=42 ms; chemical shift 200 Hz; chemical exchange 200 rad/s; T2 of the magnetization transfer pool 7.7 μs; magnetization transfer exchange rate 51 Hz; pool A population 83.1%; pool B population 1%; and magnetization transfer pool population 6.9%. The other parameters were the same as those described above with reference to generation of FIGS. 11A-11F. As before, simulated data were fitted to Eq. (14) and to the conventional model of Eq. (13).

Figure 12A:
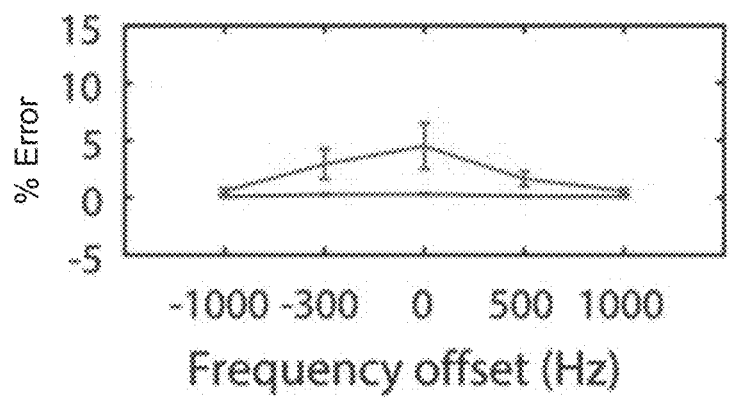
FIGS. 12A-12F are graphs showing the maximum error percentage under various conditions of the pulse sequence, including for pulse sequences according to various embodiments of the present invention.
Figure 12B:
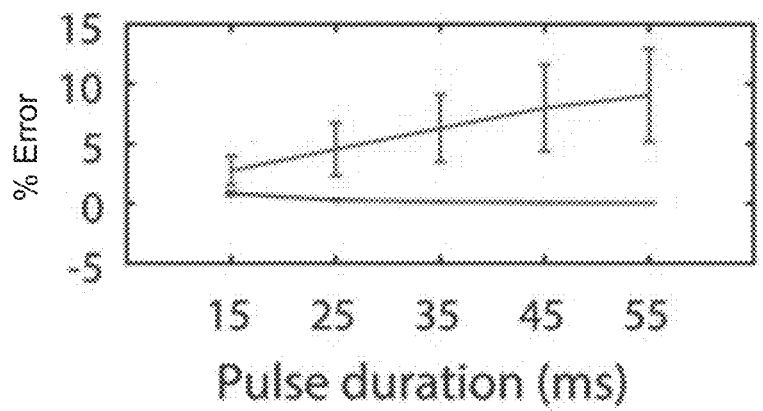
Figure 12C:
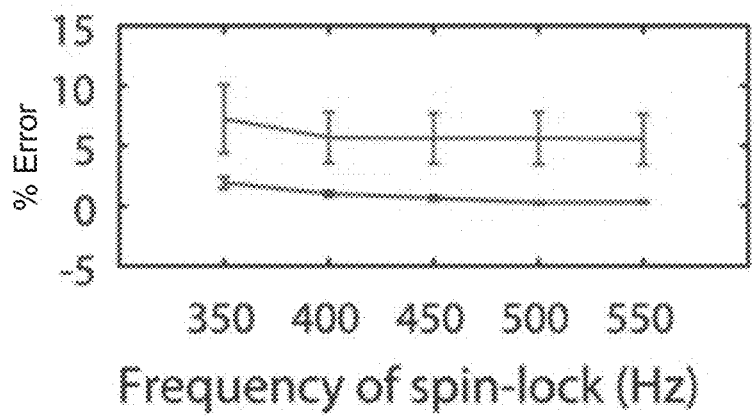
Figure 12D:
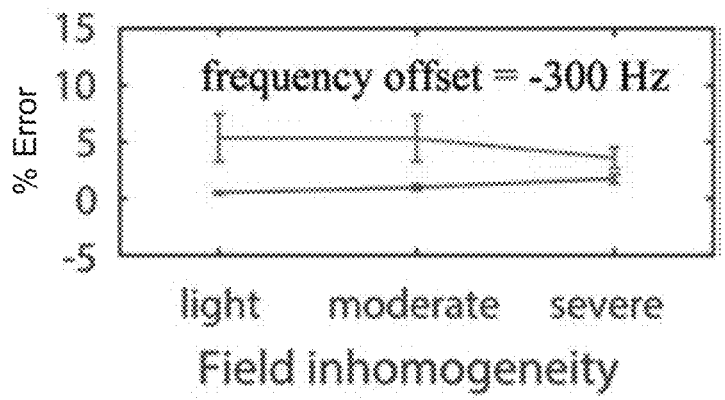
Figure 12E:
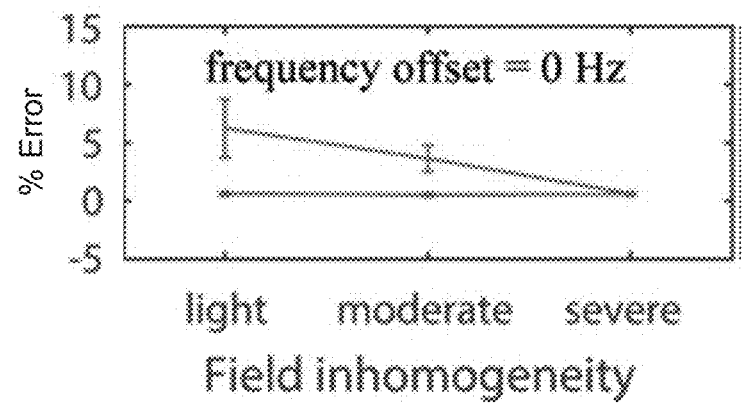
Figure 12F:
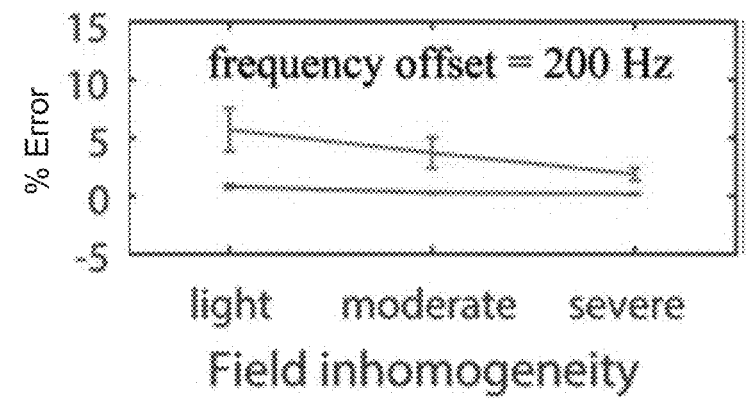

FIGS. 12A-12F are graphs showing the maximum error (%) computed using Eq. (20) under various scenarios. Blue lines show results for fitting to the modified relaxation model of Eq. (14); red lines show results for fitting to the mono-exponential relaxation model of Eq. (13). In each figure, the x axis corresponds to a different variable condition of the simulation: In FIG. 12A, frequency offset from resonance is varied; in FIG. 12B, pulse duration; in FIG. 12C, frequency of spin-lock; in FIG. 12D, field inhomogeneity levels at frequency offset from resonance of −300 Hz; in FIG. 12E, field inhomogeneity levels at frequency offset of 0 Hz (on-resonance); and in FIG. 12F, field inhomogeneity levels at frequency offset of +200 Hz. As can be seen from FIGS. 12A-12F, fitting to Eq. (14) yields low error under all conditions, while the error in fitting to Eq. (13) is generally higher and exhibits significant dependence on the conditions of data acquisition.

Examples: Imaging Studies

Imaging studies were conducted using a Philips Achieva TX 3.0T scanner equipped with dual transmit (available from Philips Healthcare, Best, the Netherlands). Specific absorption rate (SAR) was maintained within FDA limits.

For phantom imaging experiments (using test objects), data was collected using an 8-channel head coil and body transmit. The acquisition sequence was a 2D fast spin echo (FSE) sequence with low-high profile.

Figures 13A, 13B, 13C, 13D, 13E:
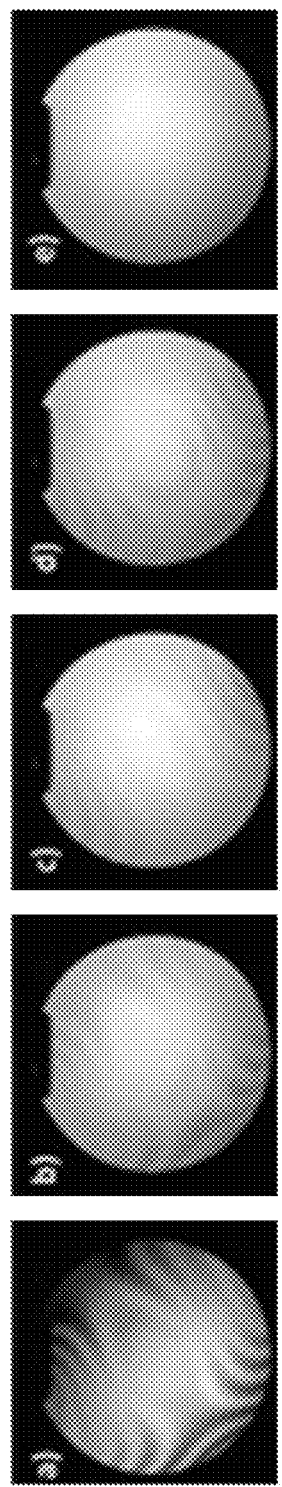
FIGS. 13A-13E show images acquired with TSL at 60 ms using a single-acquisition process with various T1rho prep sequences, including sequences according to embodiments of the present invention.

A first phantom imaging experiment was designed to demonstrate that satisfying Eq. (1) above can achieve robust compensation of B1 and B0 field inhomogeneity. In this experiment, imaging was performed in the axial plane with 15×15 cm field of view (FOV) and spin-lock frequency of 250 Hz. A 0.05 T/m shimming gradient was added along both X and Y directions to increase the off-resonance effect. FIGS. 13A-13E show images acquired with TSL at 60 ms using a single-acquisition process with various T1rho prep sequences. FIG. 13A shows an image acquired using a constant-amplitude spin-lock RF pulse with no AHP or reverse AHP. As can be seen, this image includes significant banding artifacts. FIG. 13B shows an image acquired using the maximum available B1 transmit field for the AHP and reverse AHP, significantly violating the condition specified in Eq. (1). This technique compensates for B1 inhomogeneity but still produces banding due to B0 inhomogeneity. FIG. 13C shows an image acquired using HS1 for the AHP and reverse AHP with duration $T_p$ of 30 ms, which meets the condition specified in Eq. (1) but violates the adiabatic condition. FIG. 13D shows an image acquired using HS8 for the AHP and reverse AHP with duration $T_p$ of 10 ms, which also meets the condition specified in Eq. (1) but violates the adiabatic condition. FIG. 13E shows an image acquired using HS8 for the AHP and reverse AHP with duration $T_p$ of 30 ms, which meets both the condition specified in Eq. (1) and the adiabatic condition. The image in FIG. 13E is free of banding artifacts. This demonstrates that T1rho prep sequences as described herein can reduce image artifacts resulting from inhomogeneity in the B1 and B0 fields.

Figures 14A, 14B, 14C:
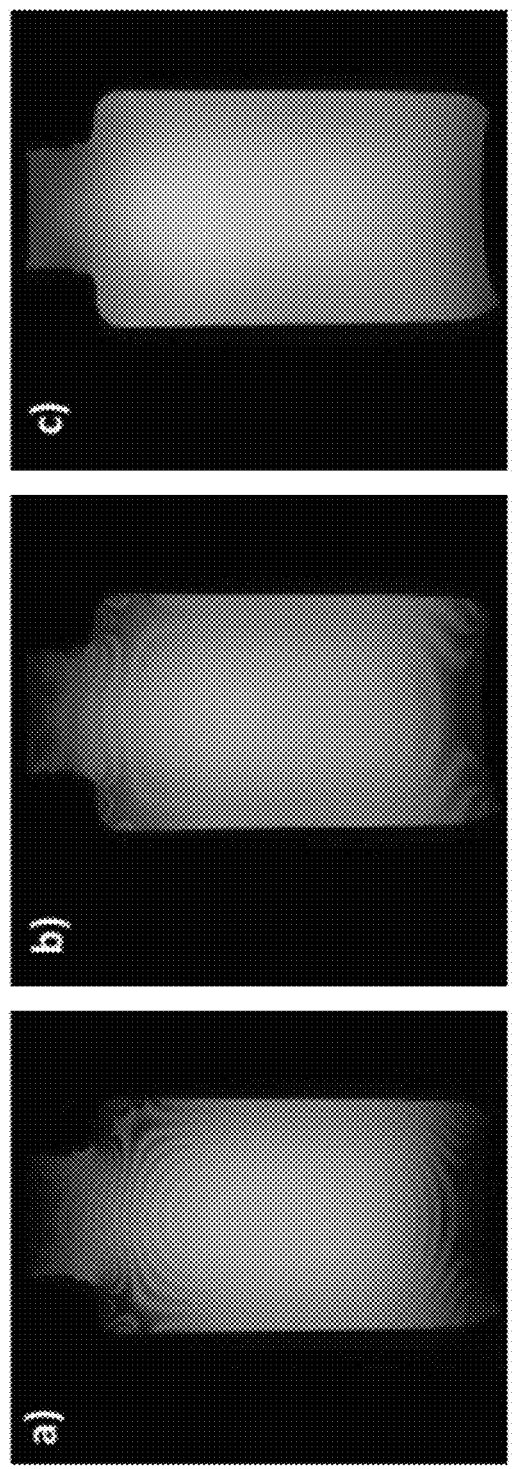
FIGS. 14A-14C show images acquired with TSL at 60 ms using various techniques, including PCCSL (FIG. 14A), Witschey's method (FIG. 14B), and a technique according to an embodiment of the present invention (FIG. 14C).

A second phantom imaging experiment was designed to compare acquisition methods described herein with the conventional Witschey method and PCCSL. For this experiment, imaging was performed in the coronal plane with 25×16 cm FOV and spin-lock frequency of 500 Hz. A 0.05 T/m shimming gradient was added along both X and Y directions to increase the off-resonance effect. FIGS. 14A-14C show images acquired with TSL at 60 ms using various techniques. FIG. 14A shows an image acquired using PCCSL. FIG. 14B shows an image acquired using Witschey's method. FIG. 14C shows an image acquired using a single-acquisition adiabatic process under conditions satisfying Eq. (1) and the adiabatic condition. As can be seen, the image in FIG. 14C is substantially free of banding artifacts, again demonstrating efficacy of T1rho prep sequences as described herein.

The first and second phantom experiments were conducted for on-resonance spin-lock. A third phantom imaging experiment was used to study the performance of techniques described herein for off-resonance spin-lock. The test object was a standard water phantom (per 1000 g $H_2O$, 1.24 g $NiSO_4$, 2.62 g NaCl). This test object was studied to compare image artifact levels between T1 rho-weighted images at TSL=80 ms for spin-lock techniques described herein and a conventional approach.

Figure 15A:
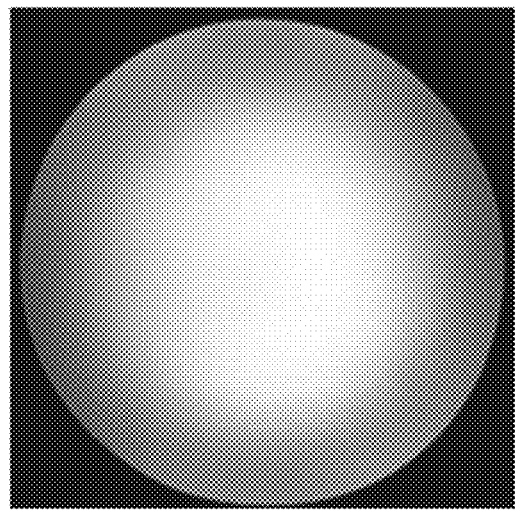
FIGS. 15A-15C show images of a test object obtained at a frequency offset of −300 Hz using a technique according to an embodiment of the present invention (FIG. 15A) and conventional techniques (FIGS. 15B and 15C).
Figure 15B:
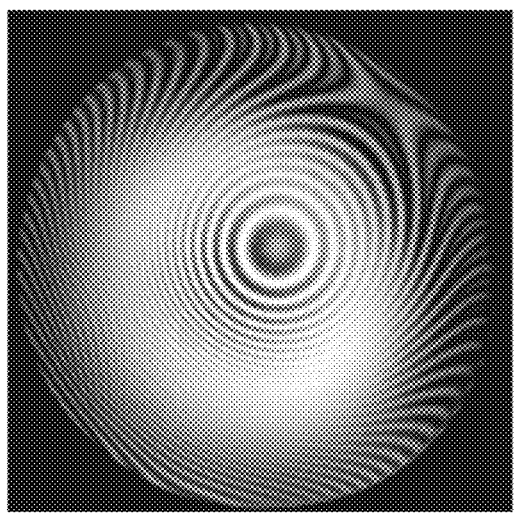
Figure 15C:
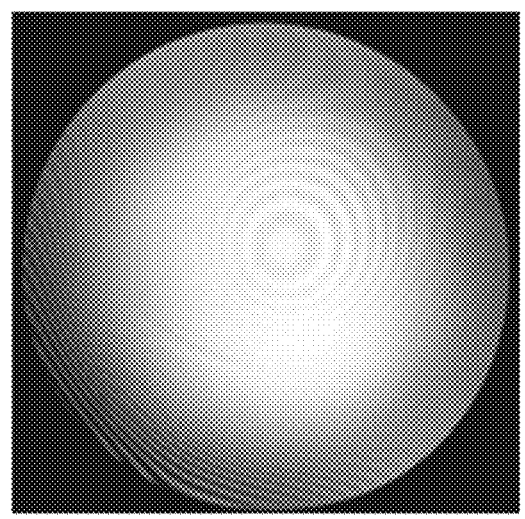

FIGS. 15A-15C show images of the test object obtained at a spin-lock frequency offset from resonance of −300 Hz. FIG. 15A shows an image generated using a pulse sequence according to an embodiment of the present invention. FIG. 15B shows an image generated using a conventional pulse sequence that produces parallel alignment between magnetization and the effective spin-lock field. FIG. 15C shows an image generated using a conventional pulse sequence that produces antiparallel alignment between magnetization and the effective spin-lock field.

Figure 16A:
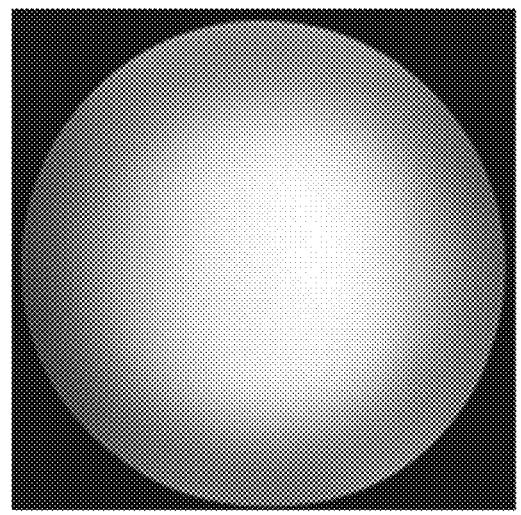
FIGS. 16A and 16B show images of a test object obtained at a frequency offset of 0 Hz (on-resonance) using a technique according to an embodiment of the present invention (FIG. 16A) and a conventional technique (FIG. 16B).
Figure 16B:
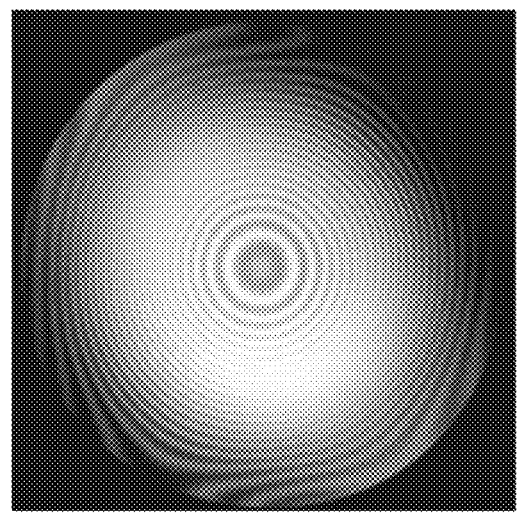

FIGS. 16A and 16B show images of the test object obtained at a frequency offset of 0 Hz (on-resonance). FIG. 16A shows an image generated using a pulse sequence according to an embodiment of the present invention. FIG. 16B shows an image generated using a conventional pulse sequence that produces parallel alignment between magnetization and the effective spin-lock field.

Figure 17A:
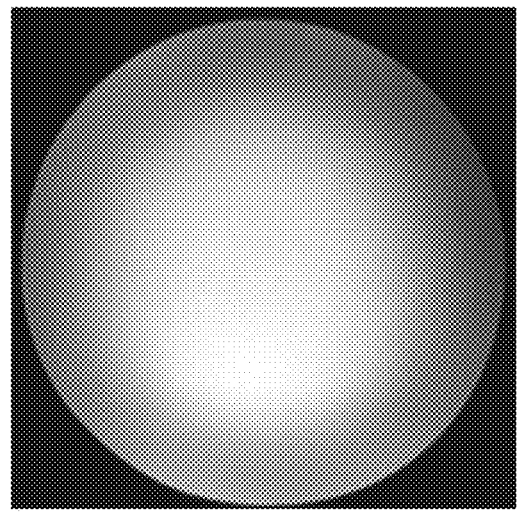
FIGS. 17A and 17B show images of a test object obtained at a frequency offset of +100 Hz using a technique according to an embodiment of the present invention (FIG. 17A) and a conventional technique (FIG. 17B).
Figure 17B:
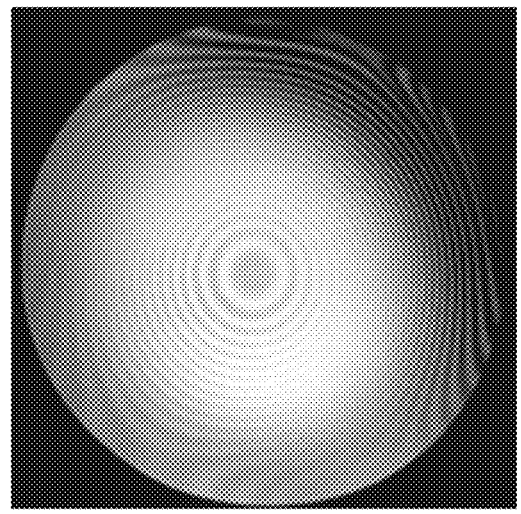

FIGS. 17A and 17B show images of the test object obtained at a spin-lock frequency offset from resonance of +100 Hz. FIG. 17A shows an image generated using a pulse sequence according to an embodiment of the present invention. FIG. 17B shows an image generated using a conventional pulse sequence that produces parallel alignment between magnetization and the effective spin-lock field.

As can be seen, images generated using a conventional pulse sequence have significant banding artifacts (as shown in FIG. 16B). Compared to the images generated using conventional pulse sequences, images generated using a pulse sequence according to an embodiment of the present invention (FIGS. 15A, 16A, 17A) are essentially artifact-free for both on-resonance and off-resonance spin-lock.

A fourth phantom imaging study was used to study quantification of T1rho using methods described herein. The test object used was an agarose hydrogel phantom made with 4% gelatin hydrogel as the test object. Data sets were collected using eight different TSLs (0 ms, 5 ms, 15 ms, 25 ms, 35 ms, 45 ms, 80 ms) at on-resonance spin-lock and off-resonance spin-lock with resonance frequency offset±150 Hz, ±300 Hz, and ±500 Hz. Data sets were collected twice, once without additional shimming and once with additional shimming gradient of 0.03 mT/m along both X and Y directions to increase the B0 field inhomogeneity. Results were compared for three groups of data sets: (1) data sets obtained using a conventional hard RF pulse cluster and quantified using the mono-exponential relaxation model of Eq. (13); (2) data sets obtained using an RF pulse cluster according to an embodiment of the present invention and quantified using the mono-exponential relaxation model of Eq. (13); and (3) data sets obtained using an RF pulse cluster according to an embodiment of the present invention and quantified using the modified relaxation model of Eq. (14).

Figure 18A:
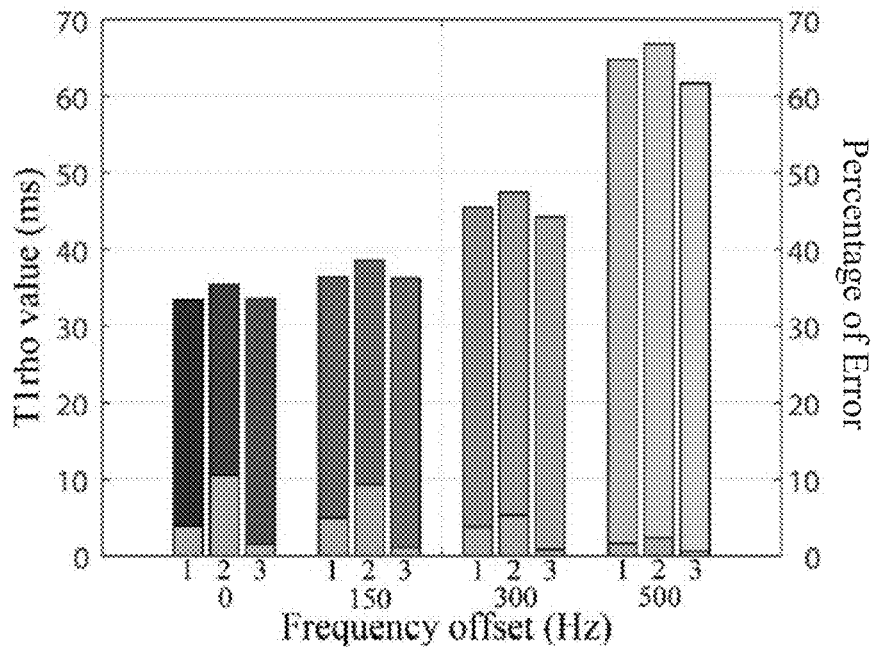
FIGS. 18A-18D show quantified T1rho values obtained from a phantom imaging study using a conventional technique and techniques according to various embodiments of the present invention.
Figure 18B:
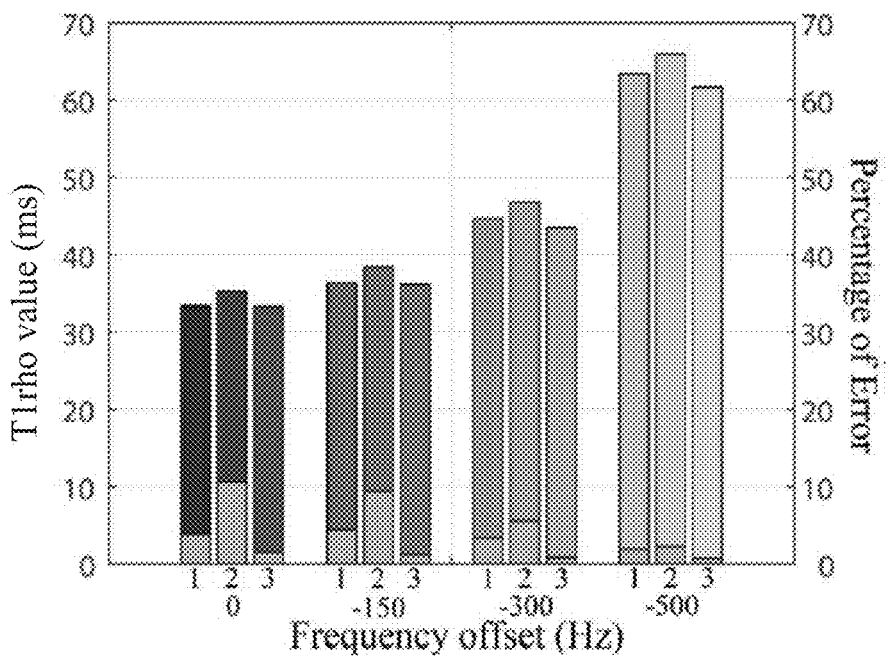
Figure 18C:
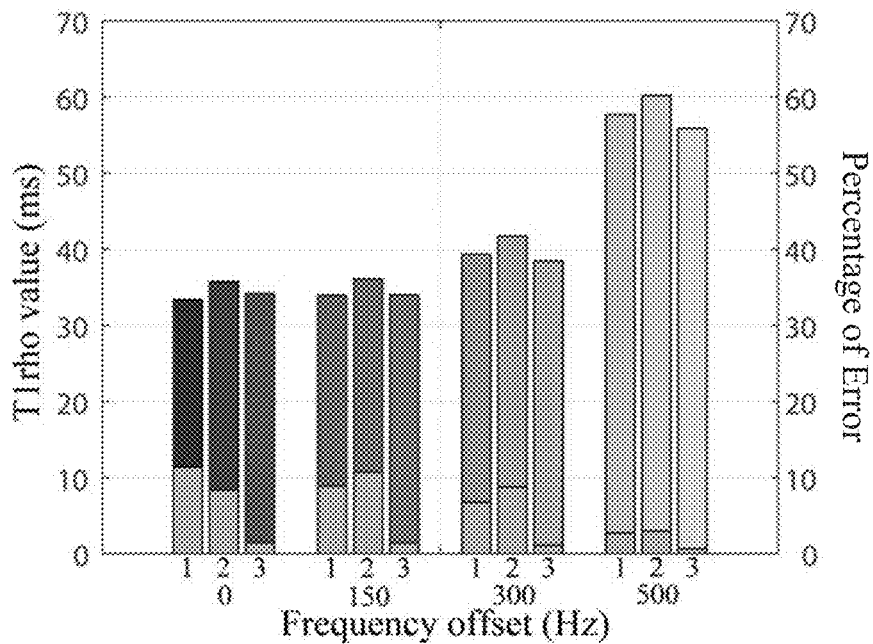
Figure 18D:
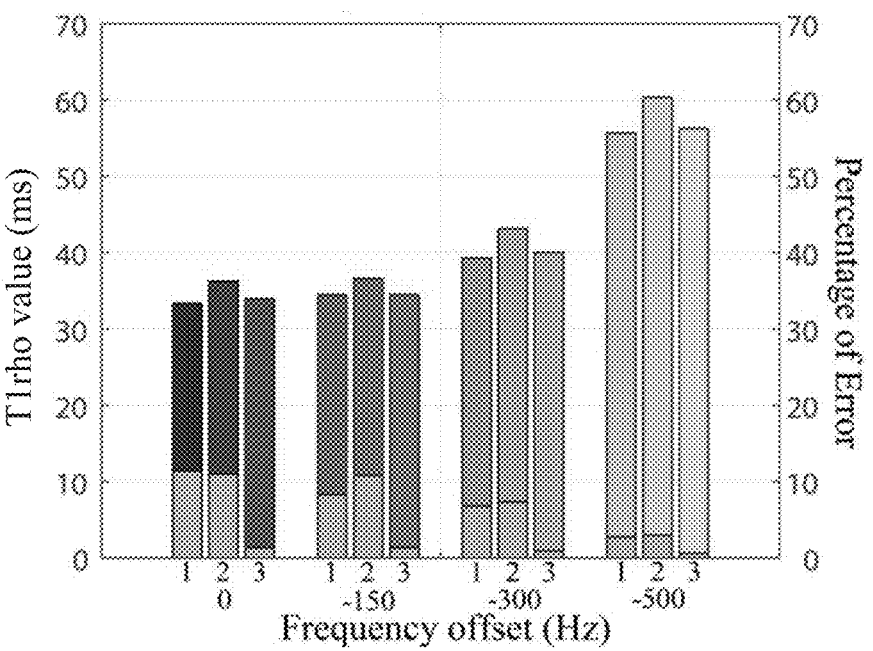

FIGS. 18A-18D show quantified T1rho values (colored bars) and percentage error (light blue bars) obtained from the fourth phantom imaging study. FIG. 18A shows results for on-resonance and off-resonance spin lock with positive resonance frequency offsets without shimming; FIG. 18B shows results for on-resonance and off-resonance spin lock with negative resonance frequency offsets without shimming; FIG. 18C shows results for on-resonance and off-resonance spin lock with positive resonance frequency offsets with shimming; and FIG. 18D shows results for on-resonance and off-resonance spin lock with negative resonance frequency offsets with shimming. In each group of bars, group (1) is on the left, group (2) in the middle, and group (3) on the right. With or without shimming, group (1) shows larger error than group (3); the error decreases with increasing offset from resonance frequency due to the reduced susceptibility to B0 field inhomogeneity. Group (2) also shows larger error compared to group (3), indicating that the conventional relaxation model is less suitable than the modified model for a spin-lock RF pulse cluster described herein.

One set of living-tissue imaging studies was conducted by imaging the livers of volunteer subjects using a 32-channel cardiac coil (made by Invivo Corp. of Gainesville, Fla.) and body transmitter. The acquisition sequence was a black-blood single shot FSE acquisition (as described in Chen et al., "Breath-hold black blood quantitative T1rho imaging of liver using single shot fast spin echo acquisition," *Quantitative Imaging in Medicine and Surgery* 6(2):168 (April 2016)). Imaging parameters included 34×24 cm FOV, single-slice acquisition with slice thickness 6 mm, echo train length 48, TR/TE 2500/20 ms, resolution 1.5×1.5 mm, SENSE acceleration factor 2, delay time for SPAIR 250 ms, double inversion recovery (DIR) with delay time 720 ms for suppression of blood signal. TSL of 0, 10, 30, and 60 ms were used, providing four images that were fitted to a mono-exponential decay model to compute a T1rho map. Imaging was performed with: (1) conventional method with no compensation for B1 RF and B0 field inhomogeneity; (2) PCCSL; (3) Witschey's method; (4) a single-acquisition adiabatic method (similar to FIG. 4) using a T1rho prep sequence as described with reference to FIGS. 2A and 2B and T1rho quantification using the mono-exponential relaxation model of Eq. (13); and (5) a dual-acquisition adiabatic method (similar to FIG. 6) and T1rho quantification using the mono-exponential relaxation model of Eq. (13). In the case of no correction, PCCSL, Witschey's method, and the single-acquisition adiabatic method, data sets were collected with two NSA (i.e., two signals collected and averaged to determine the position-encoded signal for image reconstruction), so that all imaging techniques were collected with the same scan time.

Figure 19:
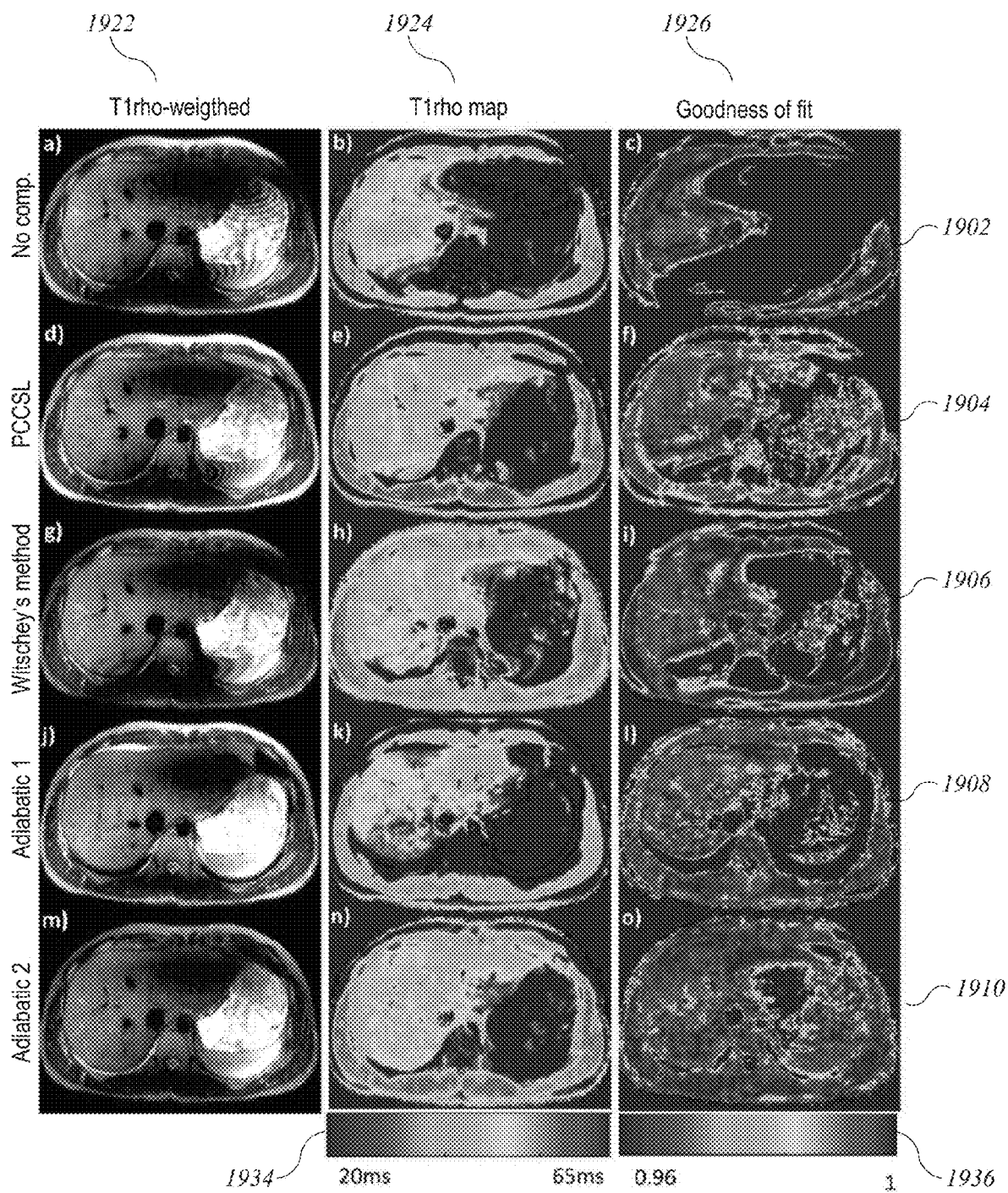
FIG. 19 shows results of the liver scans using various techniques, including techniques according to embodiments of the present invention.

FIG. 19 shows results of the liver scans using various techniques. Images in each row were produced using different techniques. Images in row 1902 were produced using conventional T1rho prep sequences with no compensation for field inhomogeneity, images in row 1904 using PCCSL, images in row 1106 using Witschey's method, images in row 1908 using a single-acquisition adiabatic method as described above, and images in row 1910 using a dual-acquisition adiabatic method as described above. In each row, the image shown in left column 1922 is a T1 rho-weighted image acquired with TSL of 60 ms, the image shown in middle column 1924 is the measured T1rho map (color scale shown at 1934), and the image in right column 1926 represents goodness of fit (color scale shown at 1936). It is noted that all images in FIG. 19 exhibit shading artifacts in the left lobe of the liver; similar artifacts were observed even in images acquired with no spin-lock pulse. Accordingly, these artifacts are believed to be a result of the reduced B1 field used in the experiment, coupled with cardiac-induced motion of the liver.

As can be seen from the T1 rho-weighted images in column 1922, significant banding artifacts occur if no correction is applied (row 1902). Banding artifacts can be reduced, but not eliminated, using PCCSL (row 1904) or Witschey's method (row 1906). Methods described herein (rows 1908, 1910) provide further improvements in image quality and images that appear substantially free of banding artifacts. As can be seen from column 1924, the single-acquisition adiabatic method (row 1908) resulted in elevated T1rho measurements relative to the dual-acquisition adiabatic method (row 1910), due to the relatively long reverse AHP (25 ms) coupled with the short T1 of liver tissue. The error is consistent with simulation results (e.g., as described above with reference to FIGS. 8A and 8B). The dual-acquisition adiabatic method (row 1910) largely corrects this error, and the goodness of fit (column 1926) is generally close to 1, demonstrating that the mono-exponential decay model can be used for T1rho quantification from the acquired images. The dual-acquisition adiabatic method (row 1910) also provides significant improvement in goodness of fit as compared to known methods (rows 1902, 1904, 1906).

Another set of living tissue studies were conducted by imaging three knees of healthy subjects using an eight-channel T/R knee coil (made by Invivo Corp. of Gainesville, Fla.). Image data were acquired using both a conventional pulse sequence and a pulse sequence according to an embodiment of the present invention, for on-resonance and off-resonance spin-lock at a number of resonance frequency offsets, including ±30 Hz, ±100 Hz, ±300 Hz, and ±500 Hz. In order to compare the performance between a conventional spin-lock pulse sequence and a spin-lock pulse sequence according to an embodiment of the present invention, the scans were repeated twice, once with and the other without a center frequency shift to intentionally increase B0 field inhomogeneity. As shown by Eq. (3), such center frequency shift only results in a shift of the spectrum along the frequency direction. The spins are still locked along the effective spin-lock field with a center frequency shift when using the pulse sequence according to an embodiment of the present invention. In contrast, a center frequency shift can cause failure of spin-lock and errors of T1rho quantification when using a conventional spin-lock pulse sequence. Imaging parameters included 16×15 cm FOV, single-slice acquisition with slice thickness 5 mm, TR/TE 2500/20 ms, resolution 1.0×1.0 mm, 2D fast spin echo acquisition with echo train length 20, and SPAIR for fat suppression. TSL of 0, 15, 35, 55, and 80 ms were used, providing five images that were fitted to the relaxation model. The T1rho quantification was based on Eq. (13) for on-resonance conventional spin-lock pulse sequence and Eq. (14) for off-resonance conventional spin-lock pulse sequence to account for the stationary solution from the Bloch-McConnell equation. For the pulse sequence according to an embodiment of the present invention, T1rho quantification was based on Eq. (14) for both on-resonance and off-resonance spin-lock. The adjusted R-square was used to compare the reliability of T1rho quantification between the two relaxation models, since they have different numbers of unknowns. (Higher values of adjusted R-square indicate better fitting accuracy.)

Figure 20:
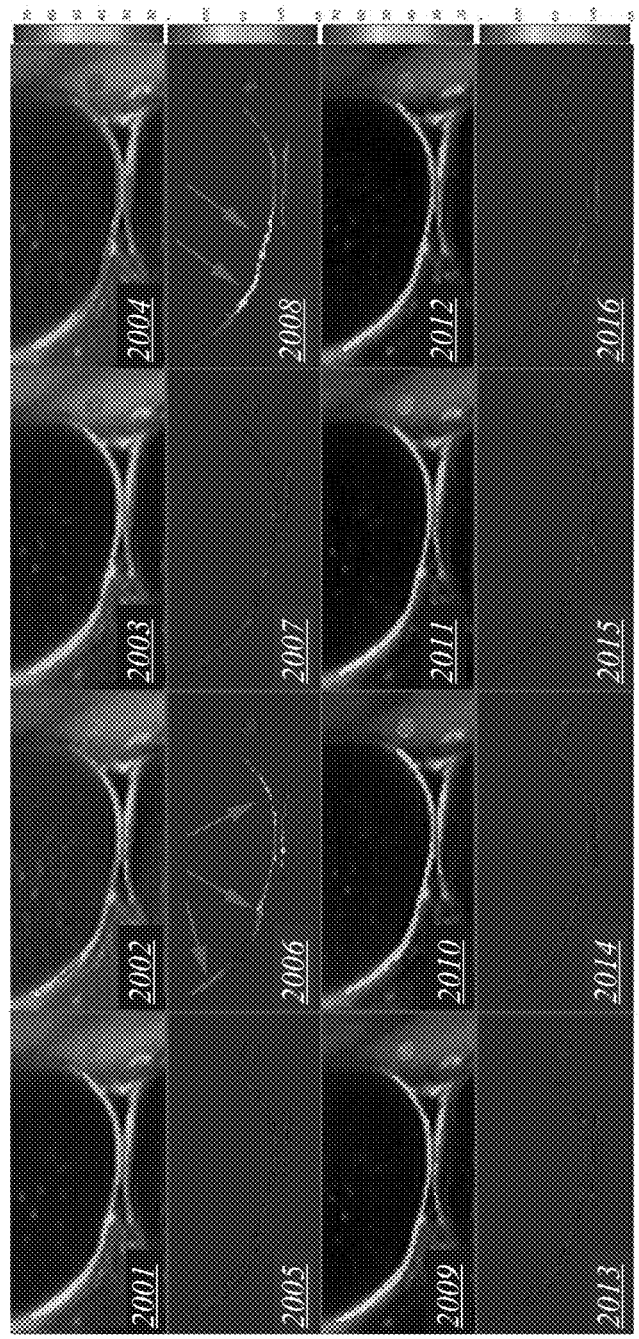
FIG. 20 shows imaging results of in vivo knee scans, for a conventional technique and for a technique according to an embodiment of the present invention

FIG. 20 shows imaging results of the in vivo knee scan. Images 2001-2004 are T1rho maps from the conventional spin-lock approach; images 2009-2012 are T1rho maps from a spin-lock approach according to an embodiment of the present invention. Images 2001 and 2009 correspond to on-resonance spin-lock without center frequency shift; images 2002 and 2010 correspond to on-resonance spin-lock with center frequency shift; images 2003 and 2011 correspond to off-resonance spin-lock (−100 Hz) without center frequency shift; and images 2004 and 2012 correspond to off-resonance spin-lock (−100 Hz) with center frequency shift. The plots below each T1rho map (plots 2005-2009 and 2013-2016) are the corresponding adjusted-R-square map. When frequency shift is not present, both the conventional spin-lockapproach and the spin-lock approach according to an embodiment of the present invention at on- or off-resonance spin-lock show good fitting. But a spin-lock approach according to an embodiment of the present invention achieves significantly improved fitting reliability (larger adjusted R-square) compared to the conventional spin-lock approach when a center shift is applied.

Figure 21:
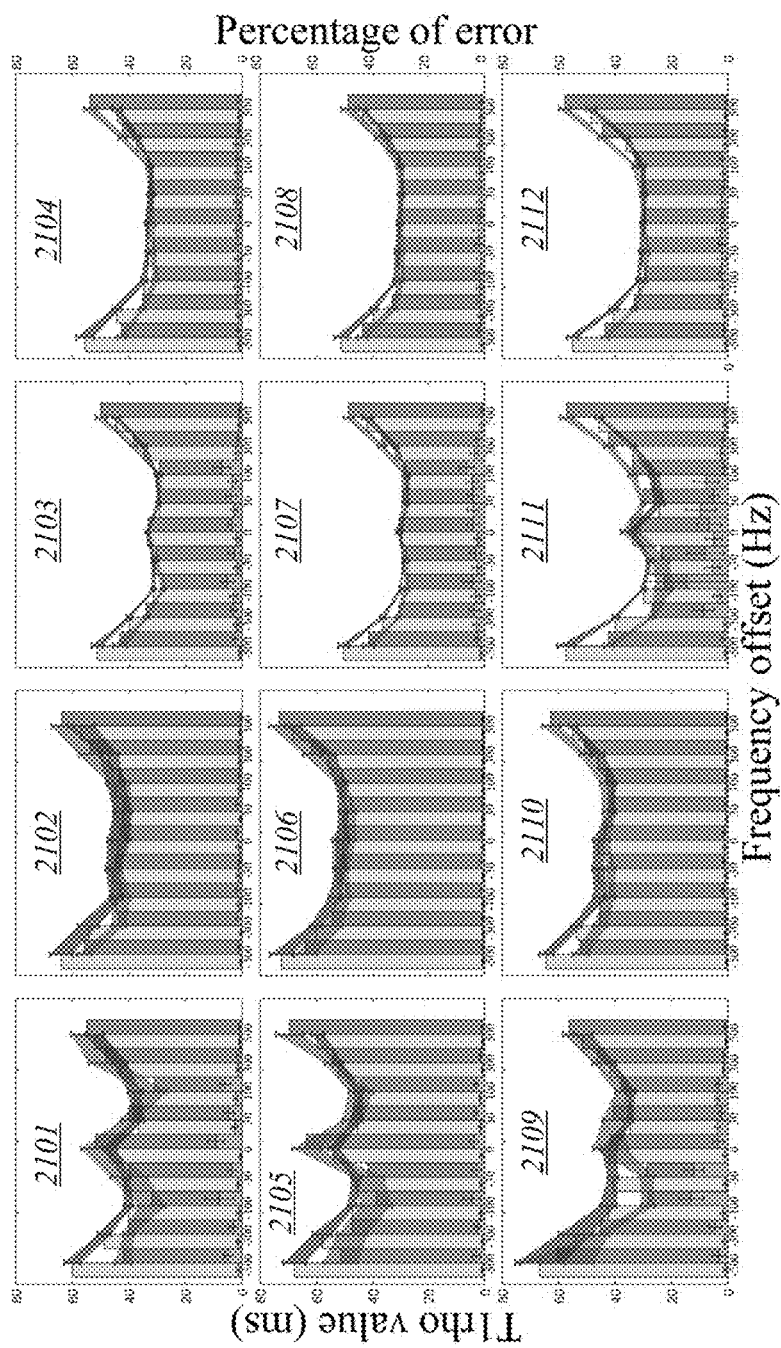
FIG. 21 shows quantification results for in vivo knee scans, using a conventional technique and a technique according to an embodiment of the present invention.

FIG. 21 shows quantification results from all three knees at on and off-resonance spin-lock. In plots 2101-2112, the mean and the standard deviation of T1rho measurement within various regions of interest (ROIs), and the mean and the standard deviation of the maximum of the fitting error calculated using Eq. (20) are plotted against frequency offset. The yellow bars and the blue belts represent the mean and the standard deviation of T1rho within the ROI without center frequency shift, and the green bars and the red belts represent the mean and the standard deviation of T1rho within the ROI with center frequency shift for increased B0 field inhomogeneity. The cyan bars at the bottom of each plot represent the mean and the standard deviation of the maximum of the fitting error calculated using Eq. (20). Plots in the first column (plots 2101, 2105, 2109) correspond to T1rho measurement from a cartilage ROI using the conventional spin-lock. Plots in the second column (plots 2102, 2106, 2110) correspond to T1rho measurement from the same cartilage ROI using a spin-lock approach according to an embodiment of the present invention. Plots in the third column (plots 2103, 2107, 2111) correspond to T1rho measurement from a muscle ROI using the conventional spin-lock. Plots in the fourth column (plots 2014, 2108, 2112) correspond to T1rho measurement from the same muscle ROI using a spin-lock approach according to an embodiment of the present invention. Note the spin-lock approach according to an embodiment of the present invention achieved significantly reduced fitting errors compared to the conventional spin-lock approach. It can be observed that the B0 field inhomogeneity induced by center frequency shift results in a shift of the T1 rho-spectrum along the frequency direction when using the spin-lock approach according to an embodiment of the present invention, which is consistent with theory (Eq. (3)). In contrast, such a trend is hardly observed for T1rho quantified using the conventional approach. Inability of the conventional approach to compensate B0 field inhomogeneity and failure of spin-lock result in unreliable T1rho quantification and distorted T1rho spectrum.

Further Embodiments

These results illustrate that methods described herein, in which a T1rho prep sequence incorporates an AHP prior to the spin-lock pulse and a reverse AHP after the spin-lock pulse, can reduce image artifacts in the presence of B1 and B0 field inhomogeneity for both on-resonance and off-resonance spin-lock. For purposes of T1rho quantification, relaxation effects during the reverse AHP (as well as effects of the stationary solution for off-resonance spin-lock) can be accounted for by using the modified relaxation model of Eq. (14). In some cases, use of a dual-acquisition approach with two T1rho prep sequences having opposite reverse AHP segments may help to preserve the accuracy of T1rho quantification for on-resonance spin-lock in cases where the adiabatic condition may not be satisfied.

It is believed that the robustness of the methods described herein may be a result of the spins being well locked along the effective B1 field during the spin-lock process. Despite the fact that the orientation of the effective B1 field is spatially varying, the spins at each spatial location are locked at the specific effective B1 field by the adiabatic methods described. In contrast, other T1rho prep RF clusters for constant-amplitude spin-lock (e.g., PCCSL and Witschey's method) were designed to mitigate artifacts, rather than directly locking the spins along the effective B1 field. Artifact mitigation techniques can result in a complicated pattern in the magnetization evolution path during spin-lock: the signal oscillates along the dimension of spin-lock (e.g., as shown in FIGS. 10A and 10B), and residual artifacts appear in the presence of significant B1 and B0 inhomogeneity.

In some embodiments with on-resonance spin-lock, T1rho values measured using techniques described herein may be affected by field inhomogeneity. This may be a result of the spins being locked in a titled angle rather than in the transverse plane. The T1rho relaxation rate at a given angle θ can be expressed as:

$$R_{1\rho}(\theta) = R_1 \cos^2\theta + R_{1\rho}^o \sin^2\theta \tag{21}$$

with $$R_{1\rho}^o = R_2 + R_{ex} \tag{22}$$

where θ is the angle given in Eq. (2) (for on-resonance spin-lock), $R_1$ and $R_2$ are the longitudinal and transverse relaxation rates of water, $R_{ex}$ is the relaxation rate related to chemical exchange, and $R_{1\rho}^o$ characterizes on-resonance T1rho relaxation rate when θ=90°. For a normal range of B0 field inhomogeneity at on-resonance imaging, $R_{ex}$ can be regarded as a constant. Eq. (21) implies that, even when image artifacts are reduced, B1 and B0 field inhomogeneity can still influence the measured T1rho value. The difference between on-resonance T1rho (=$1/R_{1\rho}^o$) and measured T1rho (=$1/R_{1\rho}(\theta)$) is symmetric about θ=0° but increases as angle θ increases.

It should also be noted that measured $R_{1\rho}(\theta)$ is highly insensitive to T1. Therefore, in situations where the B1 RF and B0 field inhomogeneity can be measured (e.g., using existing techniques), it may be feasible to correct for the difference between measured T1rho and on-resonance T1rho.

The dual-acquisition approach is effective for on-resonance T1rho imaging. However, the dual-acquisition approach may become ineffective in instances where the total off-resonance frequency term $(\alpha\omega_c + \Delta\omega_0(r))$ is significant. Provided that the adiabatic condition is satisfied, the single-acquisition approach is robust for both on-resonance and off-resonance T1rho imaging, particularly when used in combination with the modified relaxation model of Eq. (14).

In some embodiments, relaxation effects during the AHP and reverse AHP may lead to signal loss. This signal loss can be predicted using full equation Bloch simulation. For a single-acquisition adiabatic method, predicted signal loss ranges from 7% to 22% at $T_p$=15 ms and from 9% to 31% at $T_p$=25 ms, for all magnetizations with T1 in the range from 500 ms to 2000 ms and T1rho in the range from 30 ms to 100 ms. For a dual-acquisition adiabatic method, however, there is a predicted signal gain that ranges from 148% to 182% at $T_p$=15 ms and from 121% to 172% at $T_p$=25 ms, for the same range of T1 and T1rho.

In some embodiments using a dual-acquisition adiabatic approach, it may be desirable to make the durations of the AHP and reverse AHP as short as possible, in order to avoid losses in signal-to-noise ratio or long scan times.

Another approach is to incorporate a short hard pulse in place of the reverse AHP, to tip the magnetization back to the longitudinal direction after spin-lock. In practice, this approach appears to be sub-optimal for artifact correction, which may be because the tilt angle of the magnetization is spatially varying at the end of spin-lock so that it cannot be fully flipped to the longitudinal direction by the hard pulse. Accordingly, a reverse AHP after spin-lock is preferred. As long as the adiabatic condition is satisfied such that the magnetization is tipped into the effective spin-lock field after the AHP, the effect of T1 and T2 relaxation during the reverse AHP can be accounted for by modifying the relaxation model to include an extra term as described above with reference to Eq. (14). Simulation studies of the magnetization evolution during the reverse AHP indicate that Eq. (14) provides a reasonable approximation across a variety of scenarios.

While the invention has been described with reference to specific embodiments, those skilled in the art will appreciate that numerous modifications are possible. For example, the pulse sequence parameters described above can be modified, and additional pulse sequences can be incorporated as desired. Other modulation waveforms can be applied to define the AHP and/or reverse AHP provided that the adiabatic condition and the condition of Eq. (1) are satisfied or approximately satisfied. Single-acquisition or dual-acquisition approaches can be implemented.

It should also be understood that although the present description makes specific reference to T1rho as a parameter of interest, T1rho is not the only parameter that is studied using spin-lock RF pulse clusters. Accordingly, techniques described herein are not limited to T1rho imaging; they can also be applied in other imaging technologies based on spin-lock.

Thus, although the invention has been described with respect to specific embodiments, it will be appreciated that the invention is intended to cover all modifications and equivalents within the scope of the following claims.

What is claimed is:

1. A method of generating an image using a magnetic resonance imaging (MM) apparatus, the method comprising:
   applying a magnetization prep sequence that includes an adiabatic half passage, a constant-amplitude spin-lock RF pulse having a spin-lock time, and a reverse adiabatic half passage, wherein an RF amplitude of the adiabatic half passage and the reverse adiabatic half passage is equal to a spin-lock amplitude;
   performing an acquisition sequence to acquire a data set; and
   generating image data based on the data set, the image data indicative of a spatial distribution of a spin-lock based imaging biomarker for each of a plurality of locations within a region of interest of a subject.

2. The method of claim 1 wherein the spin-lock based imaging biomarker is T1rho.

3. The method of claim 1 wherein the adiabatic half passage has an amplitude modulation defined based on a hyperbolic secant function and a frequency modulation defined based on a hyperbolic tangent function.

4. The method of claim 3 wherein the adiabatic half passage is based on an HSn pulse.

5. The method of claim 1 wherein the magnetization prep sequence locks spins at each spatial location within the region of interest to an effective magnetic field at that spatial location.

6. The method of claim 1 wherein the reverse adiabatic half passage is a time-reversed version of the adiabatic half passage.

7. The method of claim 1 wherein the constant-amplitude spin-lock RF pulse has a frequency that is on-resonance with a resonant frequency of interest.

8. The method of claim 1 wherein the constant-amplitude spin-lock RF pulse has a frequency that is off-resonance by an offset Δf from a resonant frequency of interest.

9. The method of claim 8 wherein the offset Δf is negative.

10. The method of claim 8 wherein the offset Δf is positive.

11. The method of claim 1 wherein the magnetization prep sequence satisfies the condition that $\omega_1^{max}=\omega_{sl}$, where $\omega_1(t)=\gamma B_1(t)$ is an amplitude of field B1 in radians/second as a function of time (t), γ is a gyromagnetic ratio for a nuclear species of interest, $\omega_1^{max}$ is an expected maximum B1 amplitude of the adiabatic half passage and reverse adiabatic half passage in radians/second, and $\omega_{sl}$ is an expected constant spin-lock frequency in radians per second.

12. The method of claim 1 wherein the region of interest comprises a tissue of a patient.

13. A magnetic resonance imaging (MRI) system comprising:
an MRI apparatus having a magnet, a gradient coil, and one or more radiofrequency (RF) coils; and
a computer communicably coupled to the MRI apparatus, the computer having a processor, a memory, and a user interface, the processor being configured to perform a method comprising:
operating the Mill apparatus to apply a magnetization prep sequence that includes an adiabatic half passage, a constant-amplitude spin-lock RF pulse having a spin-lock time, and a reverse adiabatic half passage, wherein an RF amplitude of the adiabatic half passage and the reverse adiabatic half passage is equal to a spin-lock amplitude;
operating the MM apparatus to perform an acquisition sequence and acquire a data set; and
generating image data based on the data set, the image data indicative of a spatial distribution of a spin-lock based imaging biomarker for each of a plurality of locations within a region of interest of a subject.

14. The MRI system of claim 13 wherein the spin-lock based imaging biomarker is T1rho.

15. The MM system of claim 13 wherein the adiabatic half passage has an amplitude modulation defined based on a hyperbolic secant function and a frequency modulation defined based on a hyperbolic tangent function.

16. The MM system of claim 15 wherein the adiabatic half passage is based on an HSn pulse.

17. The MRI system of claim 13 wherein the magnetization prep sequence locks spins at each spatial location within the region of interest to an effective magnetic field at that spatial location.

18. The MM system of claim 13 wherein the reverse adiabatic half passage is a time-reversed version of the adiabatic half passage.

19. The MRI system of claim 13 wherein the constant-amplitude spin-lock RF pulse has a frequency that is on-resonance with a resonant frequency of interest.

20. The MRI system of claim 13 wherein the constant-amplitude spin-lock RF pulse has a frequency that is off-resonance by an offset 4f from a resonant frequency of interest.

21. The MRI system of claim 20 wherein the offset 4f is negative.

22. The MRI system of claim 20 wherein the offset 4f is positive.

23. The MM system of claim 13 wherein the magnetization prep sequence satisfies the condition that $\omega_1^{max}=\omega_{sl}$, where $\omega_1(t)=\gamma B_1(t)$ is the amplitude of field B1 in radians/second as a function of time (t), γ is the gyromagnetic ratio for a nuclear species of interest, $\omega_1^{max}$ is an expected maximum B1 amplitude of the adiabatic half passage and reverse adiabatic half passage in radians/second, and $\omega_{sl}$ is the expected constant spin-lock frequency in radians per second.

24. The MRI system of claim 13 wherein the region of interest comprises a tissue of a patient.

25. A method of quantifying a relaxation parameter for a region of interest within a subject, the method comprising:
performing a plurality of image generation operations using a magnetic resonance imaging (MRI) apparatus, wherein each image generation operation includes:
applying a magnetization prep sequence that includes an adiabatic half passage, a constant-amplitude spin-lock RF pulse having a spin-lock time (tsl), and a reverse adiabatic half passage, wherein an RF amplitude of the adiabatic half passage and the reverse adiabatic half passage is equal to a spin-lock amplitude, and wherein different ones of the plurality of image generation operations are performed using different spin-lock times tsl;
performing an acquisition sequence to acquire a data set; and
generating image data based on the data set, the image data indicative of a spatial distribution of the relaxation parameter for each of a plurality of locations within the region of interest;
fitting the image data from the plurality of image generation operations to a relaxation model; and
determining a value for the relaxation parameter based on a result of the fitting.

26. The method of claim 25 wherein the relaxation parameter is T1rho ($T_{1\rho}$).

27. The method of claim 26 wherein the relaxation model is defined by an equation:

$$M_e(tsl)=Ae^{-R_{1\rho}tsl}+B,$$

wherein:
$M_e(tsl)$ is a magnetization determined from the image data for a spin-lock time tsl;
A, B, and $R_{1\rho}$ are parameters determined by fitting the image data to the equation; and
$R_{1\rho}$ is equal to $1/T_{1\rho}$.

28. The method of claim 25 wherein the adiabatic half passage has an amplitude modulation defined based on a hyperbolic secant function and a frequency modulation defined based on a hyperbolic tangent function.

29. The method of claim 28 wherein the adiabatic half passage is based on an HSn pulse.

30. The method of claim 25 wherein the magnetization prep sequence locks spins at each spatial location within the region of interest to an effective magnetic field at that spatial location.

31. The method of claim 25 wherein the reverse adiabatic half passage is a time-reversed version of the adiabatic half passage.

32. The method of claim 25 wherein the constant-amplitude spin-lock RF pulse has a frequency that is on-resonance with a resonant frequency of interest.

33. The method of claim 25 wherein the constant-amplitude spin-lock RF pulse has a frequency that is off-resonance by an offset Δf from a resonant frequency of interest.

34. The method of claim 33 wherein the offset Δf is negative.

35. The method of claim 33 wherein the offset Δf is positive.

36. The method of claim 25 wherein the magnetization prep sequence satisfies the condition that $\omega_1^{max}=\omega_{sl}$, where $\omega_1(t)=\gamma B_1(t)$ is the amplitude of field B1 in radians/second as a function of time (t), γ is the gyromagnetic ratio for a nuclear species of interest, $\omega_1^{max}$ is an expected maximum B1 amplitude of the adiabatic half passage and reverse adiabatic half passage in radians/second, and $\omega_{sl}$ is the expected constant spin-lock frequency in radians per second.

37. The method of claim 25 wherein the region of interest comprises a tissue of a patient.

\* \* \* \* \*